(12) United States Patent
Locke et al.

(10) Patent No.: US 11,850,126 B2
(45) Date of Patent: Dec. 26, 2023

(54) ABSORBENT NEGATIVE-PRESSURE DRESSING SYSTEM FOR USE WITH POST-SURGICAL BREAST WOUNDS

(71) Applicant: KCI Licensing, Inc., San Antonio, TX (US)

(72) Inventors: Christopher Brian Locke, Bournemouth (GB); Benjamin Andrew Pratt, Poole (GB); James Killingworth Seddon, Wimborne (GB); John R. Harper, Boerne, TX (US)

(73) Assignee: 3M Innovative Properties Company, Saint Paul, MN (US)

( * ) Notice: Subject to any disclaimer, the term of this patent is extended or adjusted under 35 U.S.C. 154(b) by 31 days.

(21) Appl. No.: 16/500,860

(22) PCT Filed: Apr. 9, 2018

(86) PCT No.: PCT/US2018/026694
§ 371 (c)(1),
(2) Date: Oct. 4, 2019

(87) PCT Pub. No.: WO2018/212849
PCT Pub. Date: Nov. 22, 2018

(65) Prior Publication Data
US 2020/0107964 A1    Apr. 9, 2020

Related U.S. Application Data

(60) Provisional application No. 62/506,873, filed on May 16, 2017.

(51) Int. Cl.
*A61F 13/00*    (2006.01)
*A61F 13/02*    (2006.01)
(Continued)

(52) U.S. Cl.
CPC ...... *A61F 13/00068* (2013.01); *A61F 13/022* (2013.01); *A61F 13/0206* (2013.01);
(Continued)

(58) Field of Classification Search
CPC ...... A61F 13/00068; A61F 2013/00536; A61F 2013/0054; A61F 13/145; A61F 13/14;
(Continued)

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 B2    3/1986
AU    745271 B2    3/2002
(Continued)

OTHER PUBLICATIONS

Louis C. Argenta, Md and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Kai H Weng
*Assistant Examiner* — Nhu Q. Tran

(57) ABSTRACT

A system for providing negative-pressure therapy to breast tissue is disclosed. In some embodiments, the system may include a dressing assembly shaped for placement on a breast, an absorbent pouch, and a negative-pressure source. The system may further include an additional dressing assembly for placement on a second breast. Various shapes and configurations of the breast dressing assemblies may be included in the system.

7 Claims, 13 Drawing Sheets

(51) Int. Cl.
*A61F 13/14* (2006.01)
*A61M 1/00* (2006.01)
(52) U.S. Cl.
CPC ........... *A61F 13/145* (2013.01); *A61M 1/913* (2021.05); *A61M 1/915* (2021.05); *A61M 1/917* (2021.05); *A61M 1/918* (2021.05); *A61M 1/98* (2021.05); *A61M 1/984* (2021.05); A61F 2013/00174 (2013.01)
(58) Field of Classification Search
CPC ........ A61M 1/90; A61M 1/71; A61M 1/0023; A61M 2210/1007
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,998,693 A * | 12/1999 | Zagame ................. A41C 3/065 450/81 |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Teaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0125258 A1* | 5/2010 | Coulthard ............. A61F 13/022 604/319 |
| 2011/0015595 A1* | 1/2011 | Robinson ................ A61M 1/90 604/319 |
| 2012/0110822 A1* | 5/2012 | Wilkes .............. A61F 13/00034 29/428 |
| 2013/0053797 A1* | 2/2013 | Locke ................... A61M 27/00 604/319 |
| 2013/0144227 A1* | 6/2013 | Locke ..................... A61M 1/74 604/318 |
| 2013/0171911 A1 | 7/2013 | Swendseid et al. |
| 2014/0163491 A1 | 6/2014 | Schuessler et al. |
| 2014/0249495 A1* | 9/2014 | Mumby ............ A61F 13/00063 604/359 |

(56) References Cited

U.S. PATENT DOCUMENTS

| | | | |
|---|---|---|---|
| 2014/0350494 A1* | 11/2014 | Hartwell | A61F 13/00068 604/319 |
| 2015/0080788 A1 | 3/2015 | Blott et al. | |
| 2015/0182677 A1* | 7/2015 | Collinson | A61F 13/022 604/319 |
| 2016/0193452 A1* | 7/2016 | Hanson | A61F 13/0253 602/52 |
| 2017/0127732 A1* | 5/2017 | Trangmar | A41C 3/0014 |
| 2019/0290499 A1* | 9/2019 | Askem | A61M 1/90 |

FOREIGN PATENT DOCUMENTS

| | | |
|---|---|---|
| AU | 755496 B2 | 12/2002 |
| AU | 2012254926 A1 | 12/2012 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 692578 A | 6/1953 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2009158123 A2 | 12/2009 |
| WO | 2010056977 A2 | 5/2010 |
| WO | 2011008497 A2 | 1/2011 |
| WO | 2013032539 A1 | 3/2013 |
| WO | 2013078214 A1 | 5/2013 |
| WO | 2014140608 A1 | 9/2014 |
| WO | 2015188003 A1 | 12/2015 |
| WO | 2017148824 A1 | 9/2017 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, Md et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, Md., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al.; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al.; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yu.N., et al.; "Active Wound Drainage", Vestnki Khirurgi, vol. 138, Issue 4, 1987, and 7 page English translation thereof.

Davydov, Yu.A., et al.; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al.; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peka, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

(56) References Cited

OTHER PUBLICATIONS

D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion for Corresponding Application No. PCT/US2018/026694, dated Jun. 18, 2018.
Japanese Notice of Rejection for Corresponding Application No. 2019563060, dated Feb. 1, 2022.

\* cited by examiner

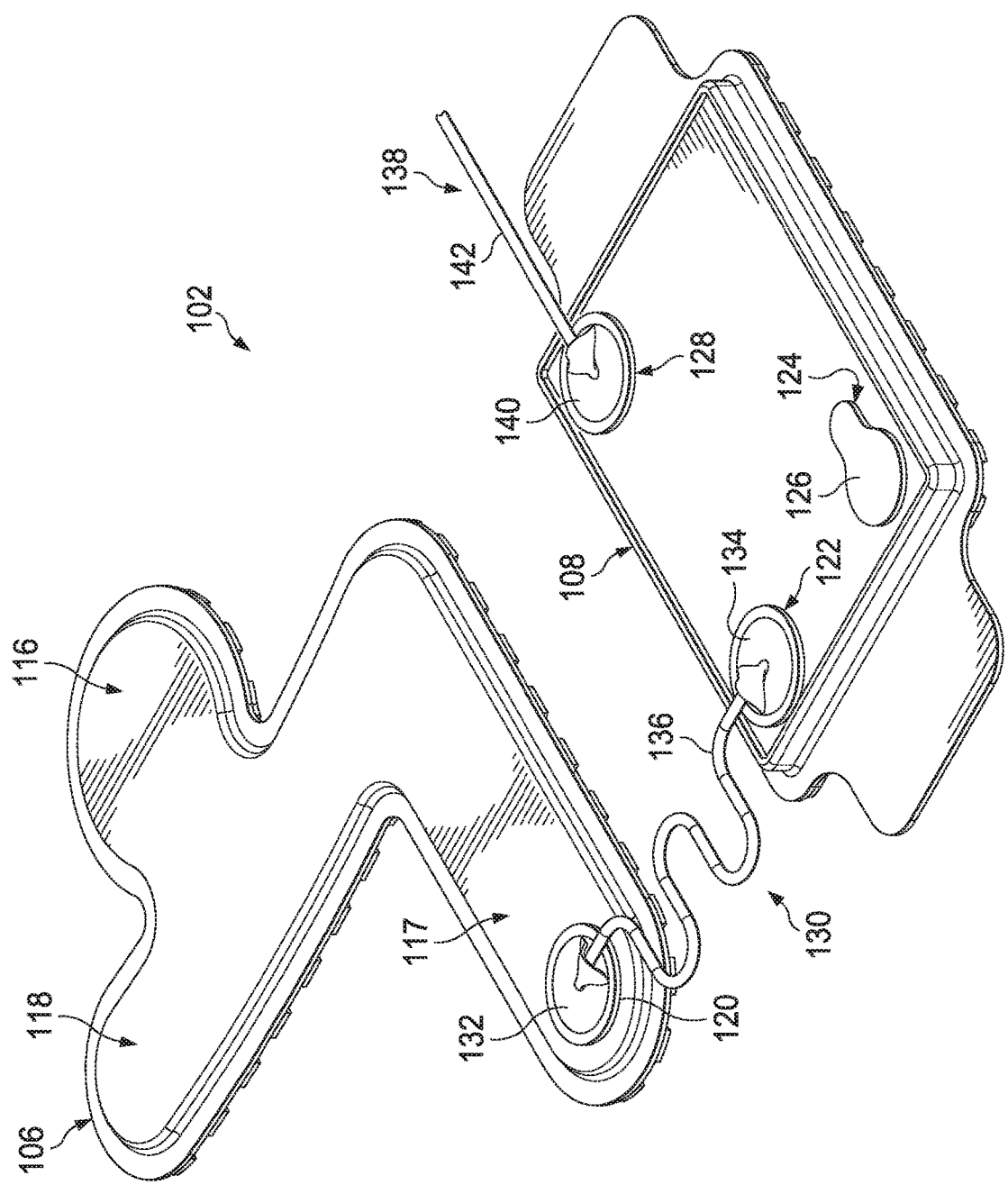
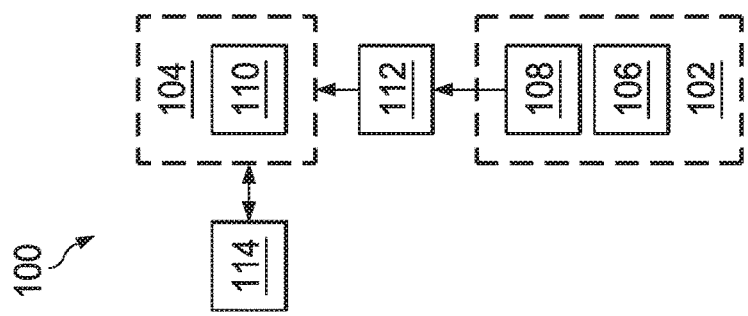

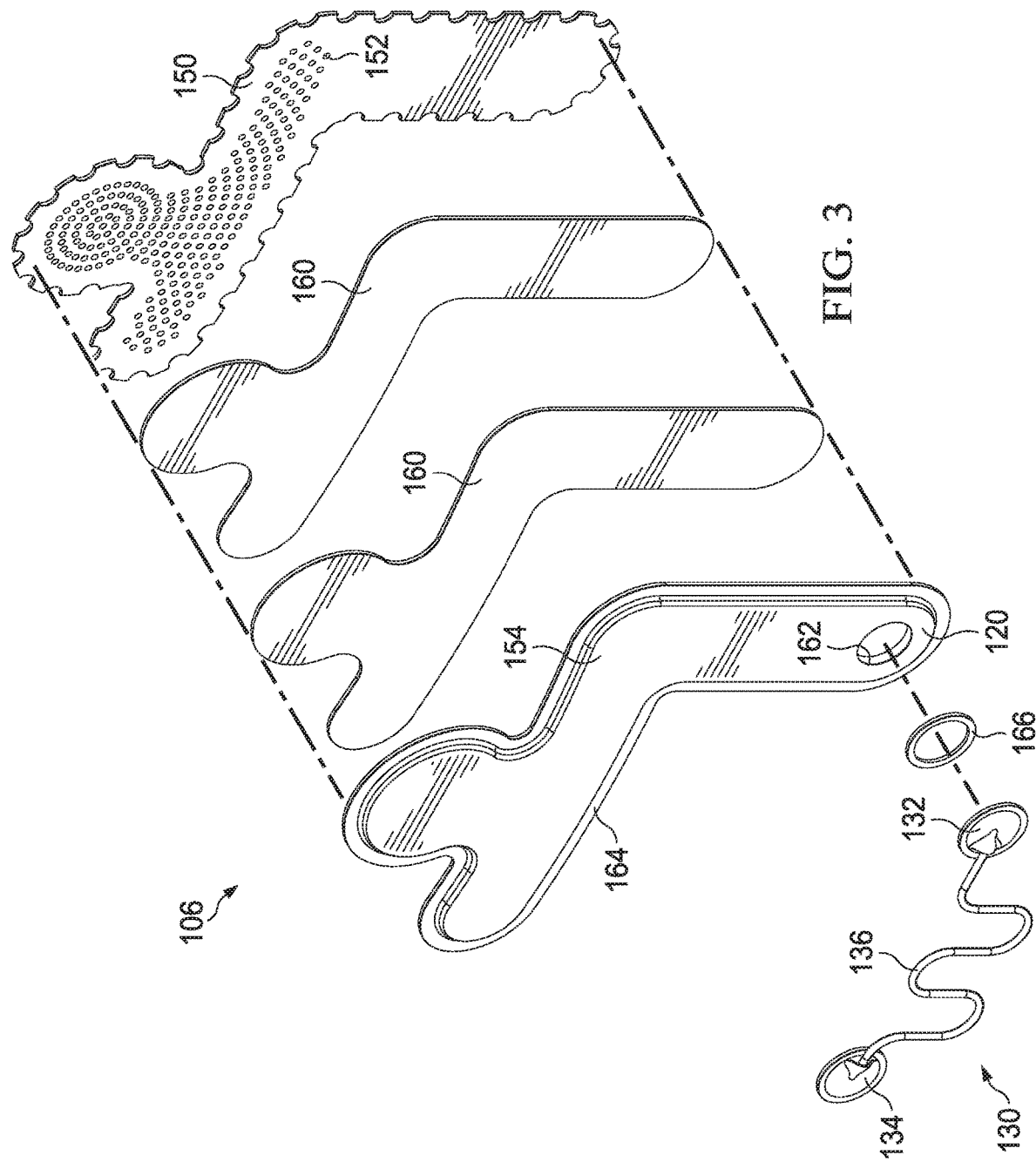

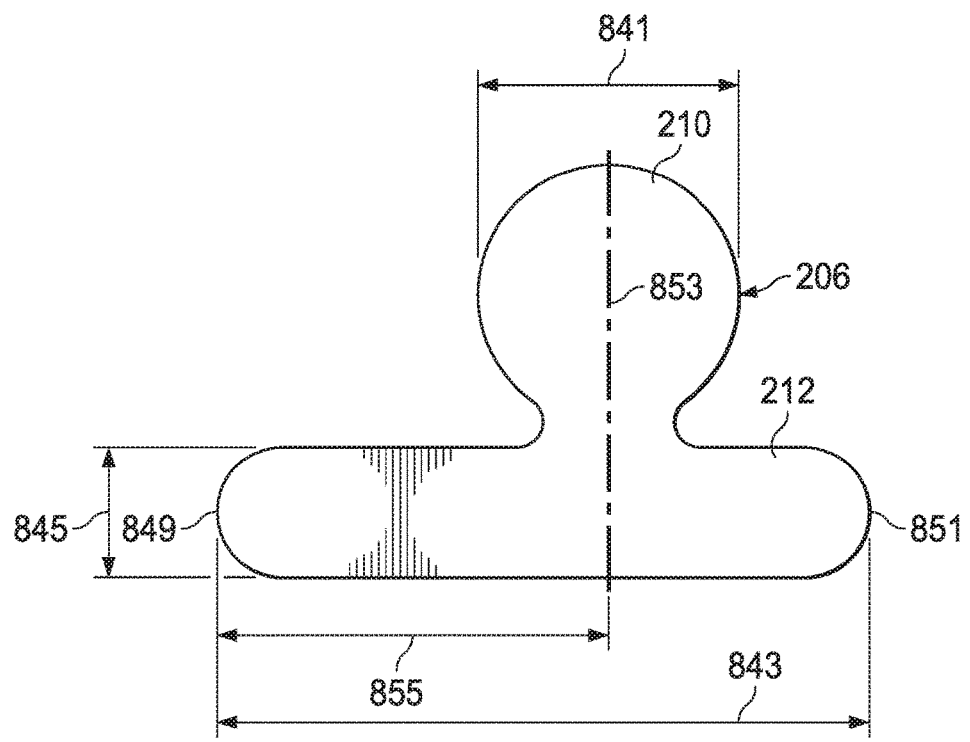
FIG. 8D
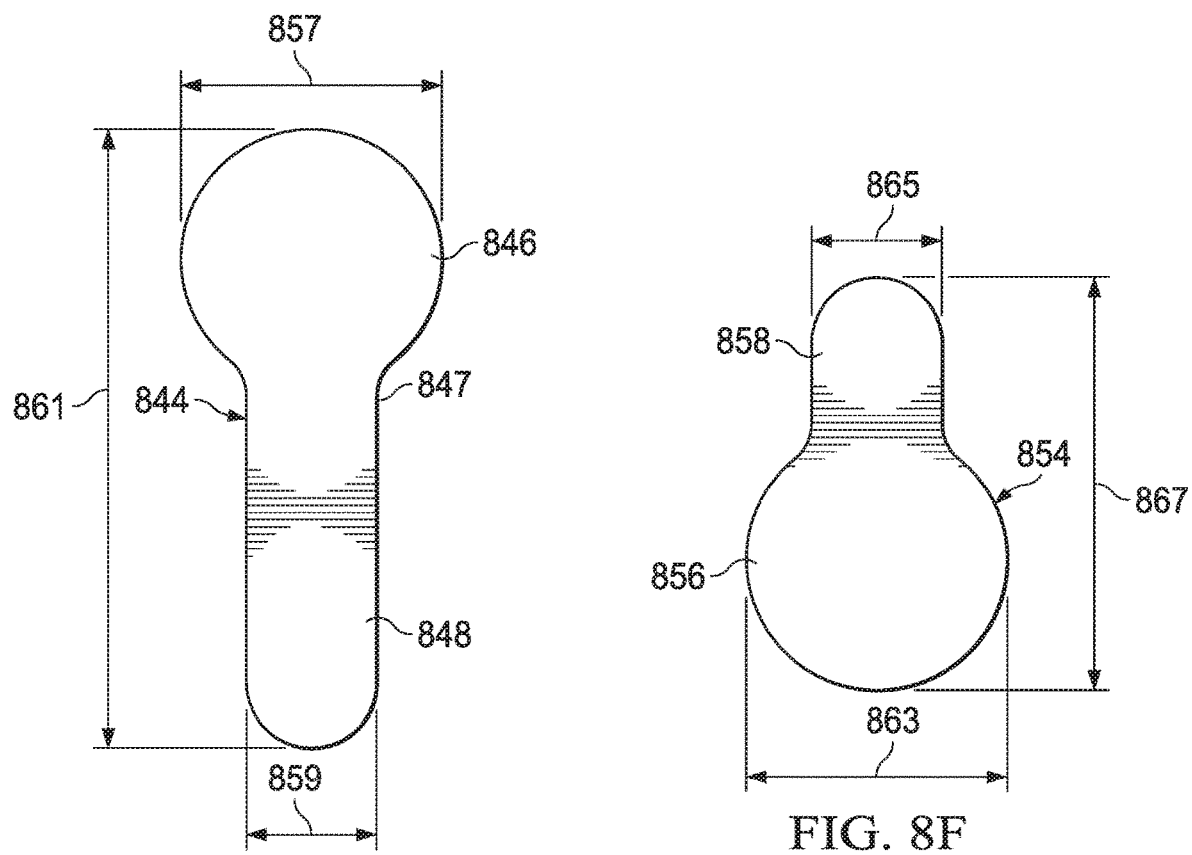
FIG. 8E
FIG. 8F

ABSORBENT NEGATIVE-PRESSURE DRESSING SYSTEM FOR USE WITH POST-SURGICAL BREAST WOUNDS

CROSS-REFERENCE TO RELATED APPLICATIONS

This application claims priority to U.S. Provisional Application No. 62/506,873, entitled "An Absorbent Negative-Pressure Dressing System for use With Post-Surgical Breast Wounds," filed May 16, 2017, which is incorporated herein by reference in its entirety.

TECHNICAL FIELD

The invention set forth in the appended claims relates generally to tissue treatment systems and more particularly, but without limitation, to negative-pressure wound treatment systems.

BACKGROUND

Millions of surgical procedures are performed each year around the world. Many of the procedures are performed as open surgery, and an increasing number are performed using minimally-invasive surgery, such as endoscopic, arthroscopic, and laparoscopic procedures. Typically, surgical procedures involve acute wounds, e.g., an incision, in the skin and related tissue. In many instances, the incision is closed at the conclusion of the procedure using a mechanical apparatus, such as staples or suture, or closed using adhesives. Thereafter, the wound is often merely covered with a dry, sterile bandage. However, there is usually more disruption than just at the epidermis. With many surgical procedures, particularly those performed using minimally-invasive techniques, much of the disruption or damage is below the epidermis, or at a subcutaneous level. The damaged tissue will need time and care to heal and poses a number of potential complications and risks including edema, seroma, hematoma, further bruising, and infection.

Clinical studies and practice have shown that reducing pressure in proximity to a tissue site, particularly a site including damaged tissue, can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for treating breast tissue in a negative-pressure therapy environment are set forth in the following summary and description, and in the appended claims. Illustrative embodiments are also provided to enable a person skilled in the art to make and use the claimed subject matter.

In some embodiments, a system for providing negative-pressure treatment may include a first dressing assembly and a negative-pressure port. The first dressing assembly may be shaped for placement on a breast and may include a crown having a substantially circular section for covering an areola and an elongate arm having a medial portion and a lateral portion and adapted to cover a wound site along an inframammary fold. The first dressing assembly may also include a dressing tissue interface, a dressing manifold, and a dressing cover. The dressing tissue interface may have a first surface adapted to adhere to the breast and perforations providing fluid paths through the dressing tissue interface. The dressing manifold may have a first side and a second side, and the first side of the dressing manifold may be disposed against a second surface of the dressing tissue interface. The dressing cover may be disposed on the second side of the dressing manifold and may have an adhesive border for sealing the dressing manifold and the dressing tissue interface to the breast. The negative-pressure port may be configured for fluid communication with a negative-pressure source.

In other example embodiments, a system for providing negative-pressure therapy to a tissue site may include a first dressing assembly, a second dressing assembly, an absorbent pouch, and a negative-pressure subsystem. The first dressing assembly may be shaped and configured to be placed on a first breast area and adapted to cover an inframammary fold, and the second dressing assembly may be shaped and configured to be placed on a second breast area and adapted to cover an inframammary fold. The absorbent pouch may include a first port and a second port. The first port may be adapted to be fluidly connected to at least one of the first dressing assembly and the second dressing assembly. The negative-pressure subsystem may be fluidly connected to the second port of the absorbent pouch and may provide negative pressure to the absorbent pouch, the first dressing assembly, and the second dressing assembly.

In yet other example embodiments, a dressing for providing therapeutic support to breast tissue of a patient may include a tissue interface, a manifold, a cover, and a port. The tissue interface may include an adhesive material on a first side and a plurality of perforations adapted to communicate negative pressure to the breast tissue. The manifold may be adapted to transmit negative pressure and acquire fluid from the breast tissue. The cover may be positioned adjacent the manifold opposite the tissue interface and may provide a fluid seal around the breast tissue. The port may be for fluidly coupling to a conduit.

In still other example embodiments, an absorbent pouch may include a tissue interface layer having an adhesive material on a first side, a manifold adapted to transmit negative pressure and to acquire fluid, an absorbent material disposed within the manifold, a cover comprising a non-adhesive film and an adhesive border, at least one port for providing fluid communication with a dressing, and at least one port cover comprising a substantially non-adherent film adapted to be removed prior to connecting a conduit to the at least one port.

In further example embodiments, a method for treating breast tissue may include applying a first dressing assembly to a first incision on at least one of an areola and an inframammary fold of a first breast of a patient, adhering an absorbent pouch to a skin surface of a second tissue site of the patient, and fluidly coupling a negative-pressure source to the absorbent pouch and the first dressing assembly.

In still further example embodiments, a dressing for breast tissue may include an incision section and a connector section. The incision section may be adapted to acquire a fluid. The connector section may be adapted to transport the fluid and may have a first side extending from a portion of the incision section and a second side having a negative-pressure interface.

In yet further example embodiments, a dressing for providing therapeutic support to a breast tissue may include a substantially circular section and an arc-shaped section having a medial portion and a lateral portion. Each of the substantially circular section and the arc-shaped section may include a tissue interface, a manifold, and a cover. The tissue interface may include a first surface adapted to adhere to the breast tissue and a plurality of perforations. The manifold may be adapted to transmit negative pressure and acquire fluid from the breast tissue. The cover may be positioned adjacent the manifold and adapted to provide a fluid seal around the breast tissue.

In still further example embodiments, a dressing for providing therapeutic support to a breast tissue may include a substantially circular section, a bridge section extending from a first side of the substantially circular section, and a port positioned on the bridge section. The port may be adapted to fluidly communicate negative pressure to the dressing.

In still further example embodiments, a dressing for providing therapeutic support to a breast tissue may include a substantially circular section and an arm section extending from a first side of the substantially circular section. The substantially circular section may include a tissue interface adapted to adhere to the breast tissue, a manifold layer, and a cover. The manifold layer may be positioned between the tissue interface and the cover. At least a portion of the arm section includes a tissue interface adapted to adhere to the breast tissue, a manifold layer, and a cover, wherein the manifold layer is positioned between the tissue interface and the cover.

In yet additional example embodiments, a system for treating a tissue site may include a dressing assembly shaped for placement on a breast and a port. The dressing assembly may include a substantially circular section and an elongate arm having a medial portion and a lateral portion and adapted to cover an inframammary fold of the breast. The port may be configured for fluid communication with a negative-pressure source.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 1 is a functional block diagram of an example embodiment of a therapy system that can deliver negative pressure to a tissue site and can manage fluids in accordance with this specification;

FIGS. 2A-2B are schematic diagrams illustrating additional details that may be associated with some example embodiments of a dressing subsystem in the therapy system of FIG. 1, FIG. 3 is an assembly view illustrating additional details that may be associated with some embodiments of the dressing of FIGS. 2A-2B;

FIG. 8D is a schematic diagram illustrating additional details that may be associated with some embodiments of the dressing of FIG. 8A;

FIG. 8E is a schematic diagram illustrating additional details that may be associated with some embodiments of the dressing of FIG. 8B;

FIG. 8F is a schematic diagram illustrating additional details that may be associated with some embodiments of the dressing of FIG. 8C;

DESCRIPTION OF EXAMPLE EMBODIMENTS

Figure 2B:
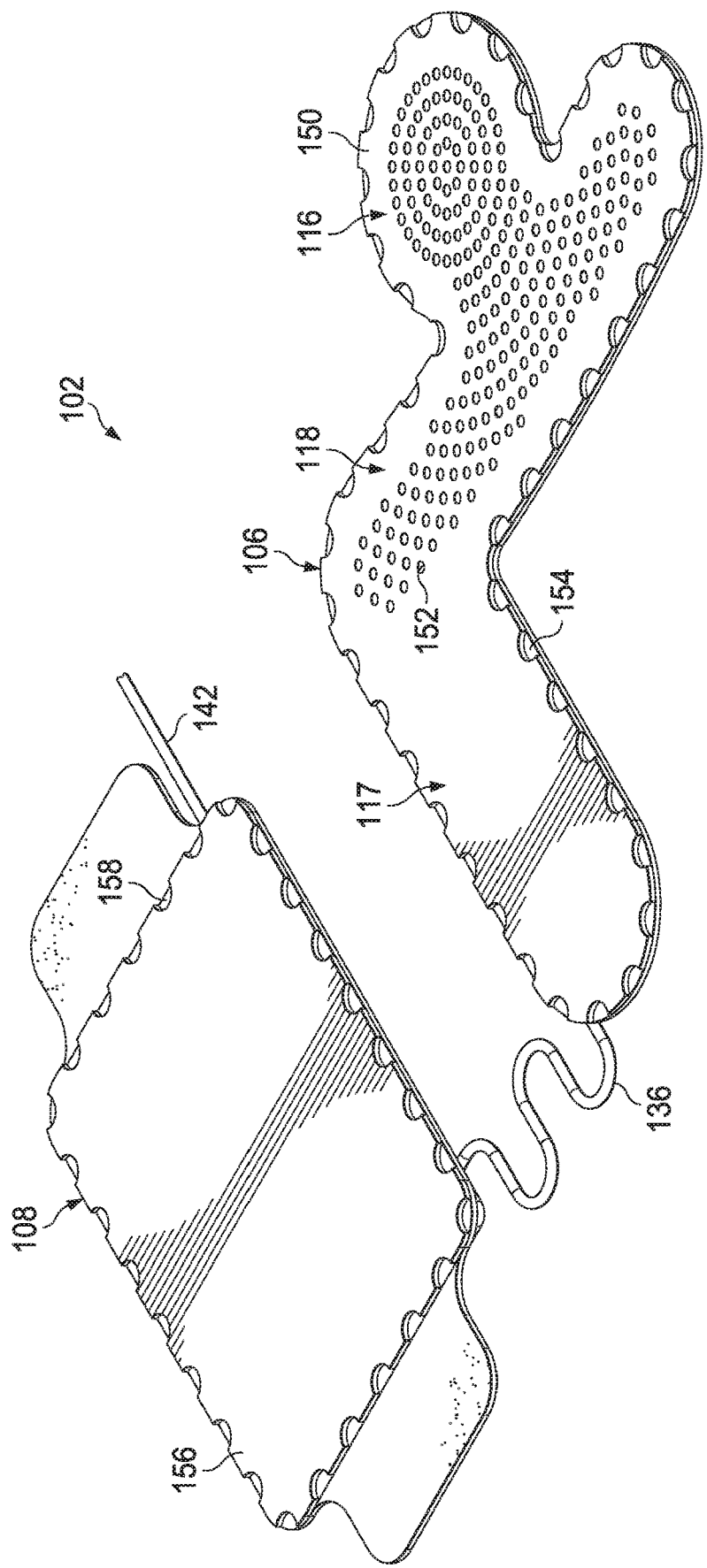

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

FIG. 1 is a simplified functional block diagram of an example embodiment of a therapy system 100 that can provide negative-pressure therapy in accordance with this specification. The therapy system 100 may include a dressing subsystem 102 and a therapy unit 104. In some embodiments, the dressing subsystem 102 may include a dressing 106 and a pouch 108. In some embodiments, the therapy unit 104 may include a negative-pressure source, such as negative-pressure source 110. The therapy system 100 may also include additional components such as a container 112 and a regulator 114, which may also be in fluid communication with the dressing subsystem 102 and the therapy unit 104.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

Components of the therapy system 100 may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 106 and the pouch 108 of the dressing subsystem 102 to each other, as well as may mechanically and fluidly couple components of the dressing subsystem 102 to the therapy unit 104 in some embodiments. In general, components of the therapy system 100 may be coupled directly or indirectly.

The therapy system 100 may include a negative-pressure supply, such as negative-pressure source 110, which may be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, the dressing subsystem 102 is illustrative of a distribution component that may be fluidly coupled to the negative-pressure source 110 of the therapy unit 104, as illustrated in FIG. 1. The dressing subsystem 102 may include a dressing, such as dressing 106, which in some embodiments may include a cover, a tissue interface, or both.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 106. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 110 of the therapy unit 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. A negative-pressure supply may also have one or more supply ports configured to facilitate coupling and de-coupling the negative-pressure supply to one or more distribution components.

Referring now primarily to FIG. 2A and FIG. 2B, the dressing subsystem 102 may be adapted to provide negative pressure from the negative-pressure source 110 of the therapy unit 104 to a tissue site, and to store fluid extracted from the tissue site. In some embodiments, the dressing 106 may be a low-profile, contoured peel-and-place dressing for application to a breast tissue. The pouch 108 may be a self-contained absorbent pouch for collecting exudates, which may also include a peel-and-place feature. In some embodiments, the dressing 106 may be a low-profile, contoured, and manifolding peel-and-place dressing which may be positioned over an incision on a breast tissue for providing negative pressure to a tissue site, such as a wound, on the breast tissue. The dressing 106 may acquire exudate and other fluids from the tissue site on the breast tissue and transport them to the pouch 108, where they may be stored within an absorbent core of the pouch 108.

FIG. 2A is a perspective top view of examples of the dressing 106 and pouch 108, illustrating additional details that may be associated with some embodiments. In some embodiments, the dressing 106, the pouch 108, or both may be of an opaque design in a discreet shade of a soft-touch pink film. The dressing 106 may be shaped and contoured to manage incisional breast wounds of a variety of shapes and sizes, inclusive of circumferential areolar incisions. For example, as shown in FIG. 2A, the dressing 106 may include one or more combinations of incision segments, such as a crown 116 and an arm 118, and a bridge segment, such as a bridge 117. For example, as illustrated in the embodiment of FIG. 2A, the arm 118 may couple the crown 116 to the bridge 117. In other embodiments, the crown 116 may be directly coupled to the bridge 117. In still other example embodiments, the dressing 106 may consist essentially of only the arm 118 and the bridge 117. Other combinations of segments may be suitable or advantageous for particular incisions. In general, an arm segment, such as the arm 118 is coupled on one end to the bridge 117 and is generally configured to cover a substantially linear incision. A crown segment, such as the crown 116, generally extends from an arm segment or a bridge and is generally configured to cover an elliptical or circular incision. For example, as illustrated in the embodiment of FIG. 2A, the crown 116 is substantially perpendicular to the arm 118. Thus, in some instances, the arm 118 may be particularly advantageous for covering a portion of an incisional wound that is perpendicular to another portion of an incisional wound, which may be covered in part by the crown 116. Additionally, the dressing 106 may be designed in at least two different orientations, one for left and right breasts, therefore allowing an individual breast or both breasts to be treated.

Referring still to FIG. 2A, the dressing 106 may include a first dressing interface 120. The pouch 108 may also include a first pouch interface 122 and a second pouch interface 124. In some embodiments, the first pouch interface 122 may be for fluidly connecting the interior components of the pouch 108 to the dressing 106. Similarly, the second pouch interface 124 of the pouch 108 may be for fluidly connecting the pouch 108 to an additional, second dressing. However, as illustrated in FIG. 2A, in cases where only a single dressing, such as dressing 106, is to be used with the pouch 108, the second pouch interface 124 may not be utilized. In such circumstances, a cover, such as first aperture cover 126 may be placed and adhered over the second pouch interface 124, in order to prevent fluid communication of the interior of the pouch 108 with an external environment. Furthermore, in some embodiments, a single pouch interface, such as first pouch interface 122, may be used for fluidly connecting multiple dressings to the pouch 108. In such embodiments, a single, Y-shaped conduit may be used for connecting the pouch 108 to the multiple dressings. For example, a conduit, such as first dressing tube 136 may include one end for connecting to the first pouch interface 122 and another end that is split in a Y-shaped configuration into two sub-conduits, each with its own end. One of the sub-conduit ends may be for connecting to the dressing 106, and a second sub-conduit end may be for connecting to a second dressing. Additionally, the pouch 108 may include a third pouch interface 128, which in some embodiments may be for fluidly connecting the pouch 108 to a source of negative pressure, such as the negative-pressure source 110 of therapy unit 104.

The dressing subsystem 102 may also include one or more tubesets for fluidly connecting the pouch 108 with the dressing 106, as well as for fluidly connecting the pouch 108 with an additional dressing if applicable. As illustrated in FIG. 2A, a first dressing tubeset 130 may include a first tube interface 132 for providing a fluid connection with the first dressing interface 120 of the dressing 106. The first dressing tubeset 130 may also include a second tube interface 134 for providing a fluid connection with the first pouch interface 122 of the pouch 108. A first dressing tube 136 may fluidly connect the first tube interface 132 and the second tube interface 134. A pouch tubeset 138 may also be included for fluidly connecting the pouch 108 to another component of the therapy system 100, such as the negative-pressure source 110 of the therapy unit 104. The pouch tubeset 138 may include a pouch tube interface 140, which may provide a fluid connection between the third pouch interface 128 of the pouch 108, and a pouch tube 142.

FIG. 2B is a bottom perspective view of the example embodiments of the dressing 106 and pouch 108 of FIG. 2A. The dressing 106 may have a low-profile, yet demonstrate high-wick absorptive properties. In some embodiments, the dressing 106 may include a dressing tissue interface 150, which may include perforations 152 in the crown 116 and the arm 118. The dressing tissue interface 150 may be covered on an outer-facing surface by a manifold (not shown) and a dressing cover 154. The dressing tissue interface 150 may be adapted to be positioned proximate to or adjacent to a tissue site, such as an incision on a patient's breast tissue. The dressing tissue interface 150 may be adapted to be positioned in fluid communication with the tissue site to distribute negative pressure to the tissue site. In some embodiments, the dressing tissue interface 150 may be positioned in direct contact with the tissue site. In some embodiments, the pouch 108 may include a pouch tissue interface 156, which may be covered on an outer-facing surface by a pouch cover 158. The pouch tissue interface 156 may be adapted to be applied to the tissue of a patient. Additionally, each of the dressing 106 and pouch 108 may be fitted with a protective release layer, which may cover the inner, tissue-facing surfaces of the dressing tissue interface 150 and the pouch tissue interface 156 prior to use of the dressing 106 and pouch 108.

Referring now primarily to FIG. 3, the various layers of the dressing 106, according to some example embodiments, may be seen in further detail. The dressing tissue interface 150 can be generally adapted to contact a tissue site. The dressing tissue interface 150 may be partially or fully in contact with the tissue site. If the tissue site is an incision or narrow wound, the dressing tissue interface 150 may be placed over the tissue site, however, in the case of deeper or wider wounds, the dressing tissue interface 150 may also partially or completely fill the wound. The dressing tissue interface 150 may take many forms, and may have many sizes, shapes, or thicknesses depending on a variety of factors, such as the type of treatment being implemented or the nature and size of a tissue site. For example, the size and shape of the dressing tissue interface 150 may be adapted to the contours of a variety of shapes of possible incisions. Moreover, any or all of the surfaces of the dressing tissue interface 150 may have projections or an uneven, coarse, or jagged profile that can induce strains and stresses on a tissue site, which can promote granulation at the tissue site.

In some embodiments, the dressing tissue interface 150 may be formed of a silicone material, such as a low-tack silicone, or a hydrogel. For example, the low-tack silicone composition may be a soft skin adhesive silicone elastomer. The low-tack nature of the dressing tissue interface 150 may provide for comfortable and low-pain adhesion of the dressing 106, and allow the dressing 106 to be positioned and repositioned as required with minimal discomfort and trauma to a patient's skin surface. In some example embodiments, the dressing tissue interface 150 may be formed of a low-tack silicone having a 180° peel adhesion strength of 0.24 N/cm to 2.76 N/cm when tested in accordance with ASTM D3330/D3330m. Additionally, the low-tack silicone may be substantially clear, which may allow for monitoring of exudate colors and levels. In some embodiments, the tissue-facing surface of the dressing tissue interface 150 may further include an adhesive layer, should additional attachment strength be necessitated or desired.

The dressing tissue interface 150 may include a plurality of apertures or openings, such as perforations 152, to allow for the transmission of negative-pressure to the tissue site and acquisition of exudate through select portions of the dressing tissue interface 150. For example, the perforations 152 may be arranged in a portion or portions of the dressing tissue interface 150 which correspond to the crown 116, the arm 118, or both, or other areas of the dressing tissue interface 150 that may align, when applied, with specific, common incision wound shapes and sizes. Preferred example embodiments of the dressing 106 may include a dressing tissue interface 150 having perforations 152 which may align with and accommodate a variety of shapes associated with mastectomy incisions, breast reduction incisions, and breast augmentation incisions. Other portions of the dressing tissue interface 150 are preferably solid, such as the portion corresponding to the bridge 117, to provide a fluid barrier between healthy tissue and exudate acquired through the perforations 152. Thus, the perforations 152 may allow for the exchange of exudates and other fluids from the tissue site into the dressing 106, where the fluids may be isolated and transported through the bridge 117.

The dressing 106 may also include a manifold, such as manifold 160, which may be positioned adjacent to the dressing tissue interface 150. The manifold 160 may be in the form of either a single layer or multiple layers, depending on the embodiment of the dressing 106 and the specific tissue site application. For example, in the example embodiment of FIG. 3, the manifold 160 may be in the form of two separate layers that are adapted to be placed against or adjacent to each other. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source.

The manifold 160 may be formed from a manifold material that may be a high-wicking manifold material, such as a capillary material or non-woven material. The high-wicking material used for the manifold 160 may allow the dressing 106 to move fluids away from the tissue site and through the dressing 106 even without the application of negative pressure. The manifold 160 may include a woven or nonwoven material. In one embodiment, the manifold 160 may be formed from Libeltex TDL2 material. In some instances, the manifold 160 may be formed from a manifold material having fibers oriented and spanning towards a negative-pressure port of the dressing 106, such as the dressing aperture 162 of the first dressing interface 120, in order to facilitate a direct flow of exudate towards the dressing aperture 162.

In some illustrative embodiments, the pathways of a manifold may be interconnected to improve distribution or collection of fluids across, or away from, a tissue site. Examples of manifold materials may include, without limitation, devices that have structural elements arranged to form flow channels, such as, for example, cellular foam, open-cell foam, porous tissue collections, liquids, gels, non-wovens, and foams that include, or cure to include, flow channels. The manifold material may be porous and may be made from foam, gauze, felted mat, or any other material suited to transport fluids. In some illustrative embodiments, a manifold may be a porous foam material having interconnected cells or pores that act as flow channels. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the manifold 160 may be a foam having pore sizes in a range of 400-600 microns. The tensile strength of the manifold 160 may also vary according to needs of a prescribed therapy. For example, the tensile strength of a foam may be increased for instillation of topical treatment solutions. In one non-limiting example, the manifold 160 may be an open-cell, reticulated polyurethane foam such as GranuFoam® dressing or VeraFlo® foam, both available from Kinetic Concepts, Inc. of San Antonio, Texas.

The manifold 160 may be either hydrophobic or hydrophilic. In an example in which the manifold 160 may be hydrophilic, the manifold 160 may also wick fluid away from a tissue site, while continuing to distribute negative pressure to the tissue site. The wicking properties of the manifold 160 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Texas Other hydrophilic foams may include those made from polyether. Other foams that may exhibit hydrophilic characteristics include hydrophobic foams that have been treated or coated to provide hydrophilicity.

In some embodiments, alternative or additional components may be incorporated into the dressing 106 as the manifold layer(s). For example, in some embodiments, a next generation wound filler or any other commercially-available filler, may be incorporated as manifold 160. As a result, a potentially-simplified dressing 106 may be achieved, which may also provide for increased bolstering or apposition forces to aid with incision closure. Additionally, in some example embodiments, the dressing 106 may also benefit from being used with additional or alternative manifold materials, which may be capable of providing apposition forces if required. For example, a manifold comprising a three-dimensional foam structure may be incorporated, which may be perforated with a pattern such that under the application of pressure, the foam structure will collapse laterally in one direction, but not the other. Thus, dressings incorporating such manifolds may be aligned along an incision site, such as an incision on breast tissue, with the direction of intended apposition force being perpendicular to the length of the incision. Applicable foam structures may include a compressed or felted GranuFoam™ commercially available from Kinetic Concepts Inc., of San Antonio, TX, USA.

The dressing cover 154 of the dressing 106 may be adapted to provide a negative-pressure environment for negative pressure delivered from the negative-pressure source 110 of the therapy unit 104 to the dressing tissue interface 150, and to assist with containing and transporting fluid extracted from the tissue site through the dressing tissue interface 150. In some embodiments, the dressing cover 154 may provide a bacterial barrier and protection from physical trauma. The dressing cover 154 may also be opaque to conceal exudate from the patient to reduce visual impact of the dressing and minimize obtrusiveness. The dressing cover 154 may also be constructed from a material that can reduce evaporative losses and provide a fluid seal between two components or two environments, such as between a therapeutic environment and a local external environment. The dressing cover 154 may be, for example, an elastomeric film or membrane that can provide a seal adequate to maintain a negative pressure at a tissue site for a given negative-pressure source. The dressing cover 154 may have a high moisture-vapor transmission rate (MVTR) in some applications. For example, the MVTR may be at least 300 g/m^2 per twenty-four hours in some embodiments. In some example embodiments, the dressing cover 154 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. In some embodiments, the dressing cover 154 may be a medium-to-high tack adhesive occluded film, such as the Inspire® 2351, commercially available from Coveris. The medium-to-high tack adhesive may act to bond the different layers of the dressing 106 together, as well as work in unison with the patient interface, such as dressing tissue interface 150, to anchor the perimeter of the dressing 106 to the patient.

The various layers of the dressing 106, such as the dressing tissue interface 150, the manifold 160, and the dressing cover 154 may be sized and configured so that each of their edges may substantially align with each other. However, in some embodiments, the dressing cover 154 of the dressing 106 may be sized so that a border around the perimeter of the dressing cover 154 extends beyond the borders of the other layers of the dressing 106, in order to be in contact with tissue of a patient. For example, the dressing cover 154 may include a cover margin 164, which may adhesively attach to a patient's skin surface.

An attachment device may be used to attach the dressing cover 154 to an attachment surface, such as undamaged epidermis, a gasket, or another cover. The attachment device may take many forms. For example, an attachment device may be a medically-acceptable, pressure-sensitive adhesive that extends about a periphery, a portion, or the entire dressing cover 154. For example, the higher-tack adhesive of the cover margin 164 of the dressing cover 154 may surround the outer profile of the other layers of the dressing 106, including the dressing tissue interface 150, and may anchor the dressing 106 in place. In some embodiments, for example, some or all of the dressing cover 154 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel. As previously mentioned, similar forms of attachment devices, specifically adhesives, may also be applied to a tissue-facing surface of the dressing tissue interface 150.

The first dressing interface 120 may include an opening, such as dressing aperture 162, for proving fluid communication between the interior components of the dressing 106 and other portions of the therapy system 100. For example, the dressing aperture 162 may allow negative pressure to be communicated from the negative-pressure source 110 of the therapy unit 104 through the first dressing tubeset 130, and through the dressing aperture 162 to the manifold 160, dressing tissue interface 150, and ultimately the tissue site of the patient. The dressing 106 may further include an attachment means, such as adhesive ring 166, for securing the first tube interface 132 of the first dressing tubeset 130 around the dressing aperture 162 to the first dressing interface 120 of the dressing cover 154.

Figure 4:
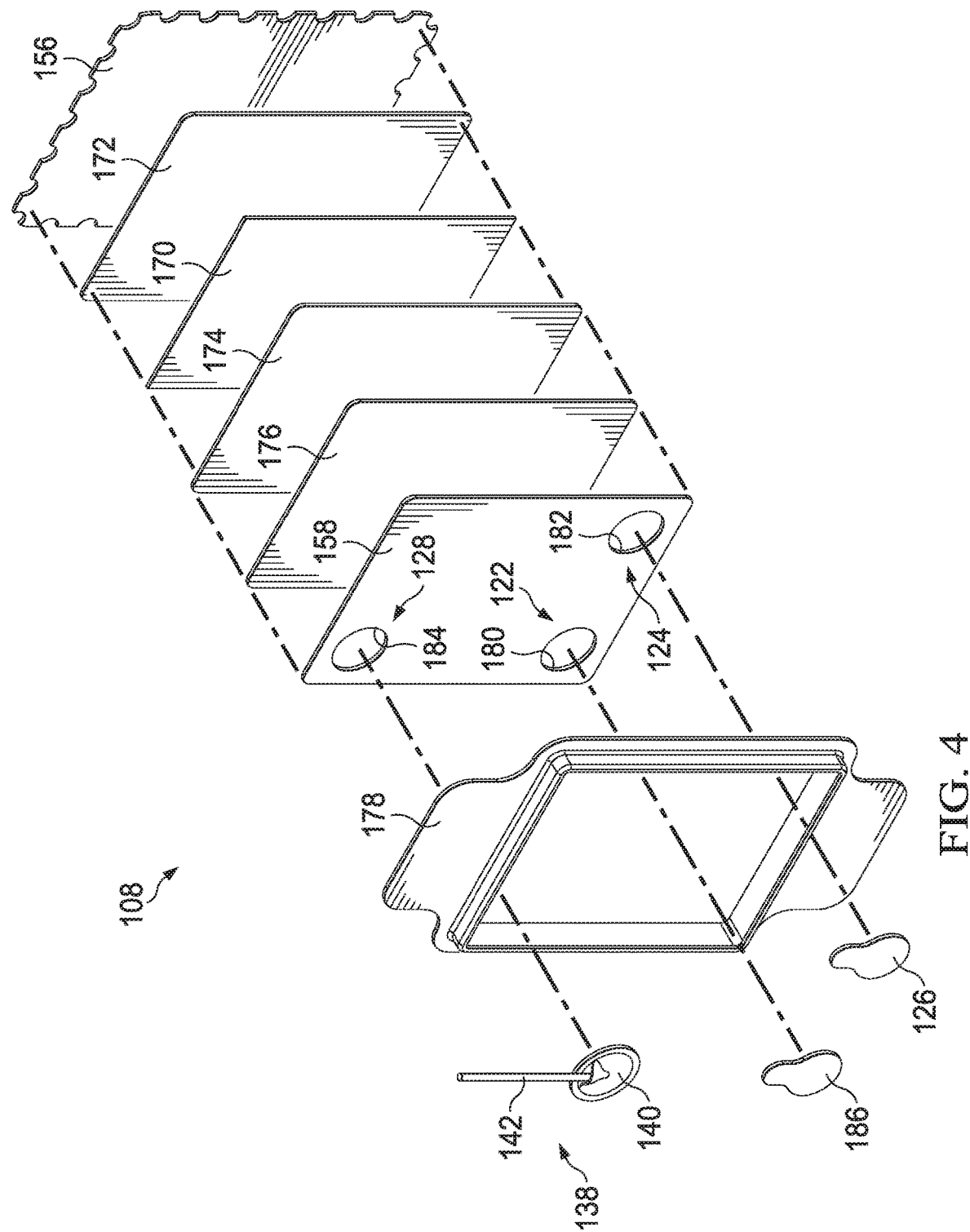
FIG. 4 is an assembly view illustrating additional details that may be associated with some embodiments of the pouch of FIGS. 2A-2B.

Referring now primarily to FIG. 4, additional details associated with an example embodiment of the pouch 108 of the dressing subsystem 102 of FIG. 2 are shown. For example, the pouch 108 may include a pouch tissue interface 156, which may be generally adapted to be placed and adhered to the surface of a patient's skin. Similarly to the dressing tissue interface 150 of the dressing 106, the pouch tissue interface 156 may take many forms, and may have many sizes, shapes, or thicknesses depending on a variety of factors, such as the type of treatment being implemented, the size or capacity of the pouch 108, or the desired location of the patient to which the pouch 108 will be attached. Thus, the size and shape of the pouch tissue interface 156, and the pouch 108 as a whole, may be adapted to the contours of a variety of body locations. The pouch tissue interface 156 may be formed from a variety of materials. In some embodiments, the pouch tissue interface 156 may be formed of a low-tack silicone material. Including a low-tack material, such as a low-tack silicone material, on the patient-facing side of the pouch 108 may provide for a comfortable and pain-free adhesion to the patient, and may allow for the pouch 108 to be positioned and repositioned as required with minimal discomfort or trauma to the patient. As discussed with respect to the dressing 106, the low-tack silicone material of the pouch tissue interface 156 may be substantially clear for allowing monitoring of colors and volumes of exudates.

In some embodiments, the pouch 108 may include an absorbent layer for receiving and storing fluids from a tissue site, which may be a super-absorbent layer 170. The super-absorbent layer 170 may be positioned between two or more manifold layers. The super-absorbent layer 170 may include one or more super-absorbent materials, such as Texsus 400-800GSM or Gelok 300GSM. For example, in some embodiments the super-absorbent layer 170 may be made substantially from Texsus 400-800GSM or Gelok 300GSM. The super-absorbent layer 170 may acquire exudate, as well as other fluids, and stabilize them, thus helping to minimize or prevent leakage.

The pouch 108 may also include two or more manifold layers, at least one of which may be positioned adjacent to the pouch tissue interface 156. For example, in the embodiment shown in FIG. 4, the pouch 108 may include three manifold layers. The first manifold layer 172 is shown positioned between the pouch tissue interface 156 and the super-absorbent layer 170. The second manifold layer 174 and the third manifold layer 176 are shown positioned adjacent to each other and between the super-absorbent layer 170 and the pouch cover 158. Similar to the manifold 160 of the dressing 106, the manifold layers of the pouch 108 may be formed from a variety of materials. In some embodiments, each manifold layer of the pouch 108 may be formed of one or more different materials from the other manifold layers of the pouch 108. In one preferred embodiment, the manifold layers 172, 174, and 176 may be formed of the same material, which may be Libeltex TDL2 material.

The pouch cover 158 may be adapted to communicate negative pressure from the negative-pressure source 110 of the therapy unit 104 through the various other layers of the pouch 108 and to the dressing 106 of the dressing subsystem 102, as well as store fluid extracted from the tissue site undergoing treatment. Similarly to the dressing cover 154 of the dressing 106, the pouch cover 158 may provide a bacterial barrier and prevent fluids and/or odors from being released from the pouch 108. The pouch cover 158 may also be constructed from a material that can reduce evaporative losses and provide a fluid seal between two components or two environments, such as between a therapeutic environment and a local external environment. The pouch cover 158 may be formed from the same or similar materials as the dressing cover 154, as previously discussed. The pouch cover 158 may be, for example, an elastomeric film or membrane that can provide a seal adequate to maintain a negative pressure at a tissue site for a given negative-pressure source. The pouch cover 158 may have a high moisture-vapor transmission rate (MVTR) in some applications. For example, the MVTR may be at least 300 g/m^2 per twenty-four hours in some embodiments. In some example embodiments, the pouch cover 158 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. In some embodiments, the pouch cover 158 may be formed from an Inspire® 2150 or 2151, 15 µm matte pink polyurethane film, which may be non-adhesive, and may be commercially available from Coveris.

The moisture transmission and evaporation facilitated by materials of the pouch cover 158 may enhance exudate capacity and thus extend product life. For example, rather than incorporating an adhesive layer on the pouch cover 158, a high-tack adhesive border, such as cover adhesive border 178, may be included to facilitate assembly and may provide high-tack adhesive anchor points for secure adhesion of the layers of the pouch 108 to a patient's skin. The cover adhesive border 178 may be placed over the pouch cover 158. As shown in FIG. 4, in some embodiments, the cover adhesive border 178 may be sized so that when placed over the pouch cover 158, the cover adhesive border 178 covers a margin around the perimeter of the pouch cover 158 as well as a portion of the patient's skin, while allowing a substantial portion of the pouch cover 158 to remain accessible to the external surface of the pouch 108. In some embodiments, the high-tack adhesive border, such as cover adhesive border 178, may be formed from, but not limited to, Inspire® 2321 or 2327, commercially available from Coveris. Additionally, in some embodiments, the cover adhesive border 178 may include two adhesive tabs which may be used to provide further adhesion to the patient or to allow the pouch 108 to be rolled and secured to itself.

Similar to the attachment of the dressing cover 154, an attachment device may be used to attach the pouch cover 158 to an attachment surface, such as undamaged epidermis or one or more of the other layers of the pouch 108, such as the third manifold layer 176 in the example embodiment of FIG. 4. As described above with respect to the dressing cover 154, an attachment device may take many forms. For example, the attachment device may be a medically-acceptable, pressure-sensitive adhesive that extends about a periphery, a portion, or the entire pouch cover 158. For example, the higher-tack adhesive of the pouch cover 158 may surround the outer profile of the other layers of the pouch 108, including the pouch tissue interface 156, and may anchor the pouch 108 in place. In some embodiments, for example, some or all of the pouch cover 158 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The pouch cover 158 may also include a region referred to as the first pouch interface 122. Additionally, the pouch cover 158 may include a second pouch interface 124 and a third pouch interface 128. The first pouch interface 122 may include an opening, such as the first pouch aperture 180, for providing fluid communication between the interior components of the pouch 108 and other components of the therapy system 100. For example, the first pouch aperture 180 may allow negative pressure to be communicated from the pouch 108 to the dressing 106 through the first dressing tubeset 130. The second pouch interface 124 may also include an opening, such as the second pouch aperture 182, which may allow for fluid communication between the pouch 108 and a second dressing through a second dressing tubeset. Furthermore, the third pouch interface 128 may include an opening, such as the third pouch aperture 184, which may allow for the pouch 108 to be in fluid communication with other components of the therapy system 100, such as the therapy unit 104 and negative-pressure source 110, through the pouch tubeset 138.

As previously mentioned, although the pouch 108 may be configured to be fluidly connected to two or more tissue dressings, in some circumstances, only one dressing, such as dressing 106, may be deployed as part of the therapy system 100. In such cases where only a single dressing is to be used with the pouch, the additional pouch interface, which may be the first pouch interface 122 or the second pouch interface 124, may not be utilized. In such instances, and depending on which of the pouch interfaces is in use, the pouch 108 may include a first aperture cover 126 and a second aperture cover 186, either of which may be applied. Furthermore, in some circumstances, for example when no dressing is connected to the pouch 108, both first aperture cover 126 and second aperture cover 186 may be adhered to the apertures of the pouch cover 158. Such circumstances may include when one or more dressings, as well as associated dressing tubesets, are being replaced. The aperture covers, including first aperture cover 126 and second aperture cover 186, may be formed from a low-tack polyurethane film or a non-adherent polyurethane film with an incorporated low-tack silicone adhesive ring. The aperture covers may further include peel tabs for easy removal. At the appropriate time, the aperture covers may be removed to allow for the fluid connection of one or more dressings, such as dressing 106, to the pouch 108 by one or more tubesets, such as first dressing tubeset 130. While the embodiment of the pouch 108 depicted in FIG. 4 includes two aperture covers to cover the two pouch apertures designed to fluidly couple dressings, a greater number of pouch apertures, and therefore aperture covers, may also be included if connecting more than two dressings to the pouch 108 is desired. Also worth noting, the multiple dressings connected to the pouch 108 are not limited to two identical dressings, and therefore, different shaped dressings may be used to treat different incisions on wounds which require a different dressing configuration, i.e., differently-sized left and right breast dressings or multiple dressings for a single mastectomy.

Figure 5A:
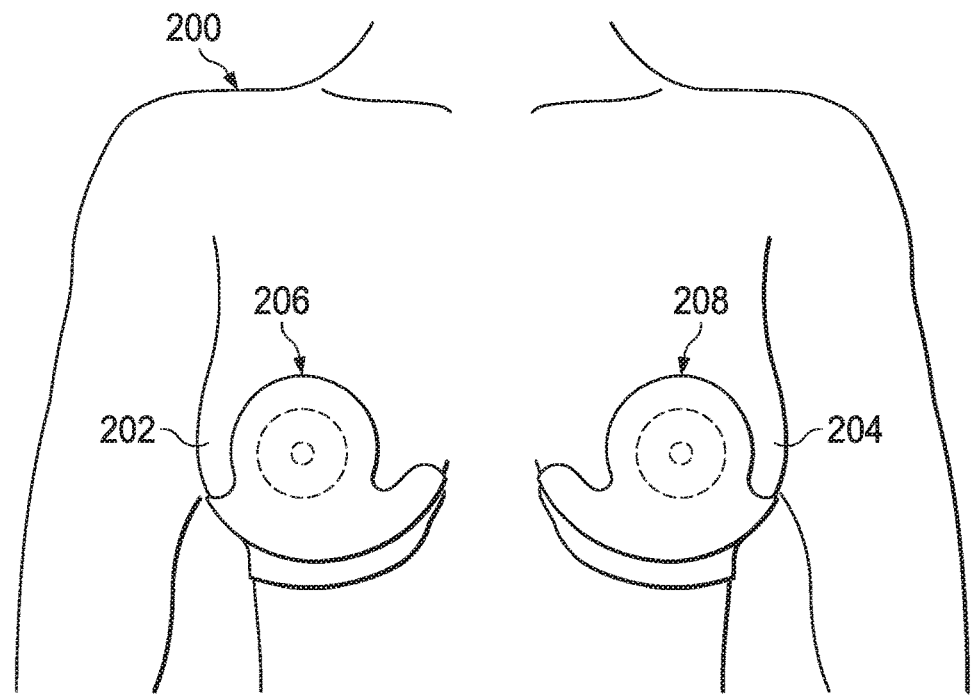
FIG. 5A is a front-facing view of example breast dressings applied to the breasts of a model simulation patient, according to one example illustrative embodiment.
Figure 5B:
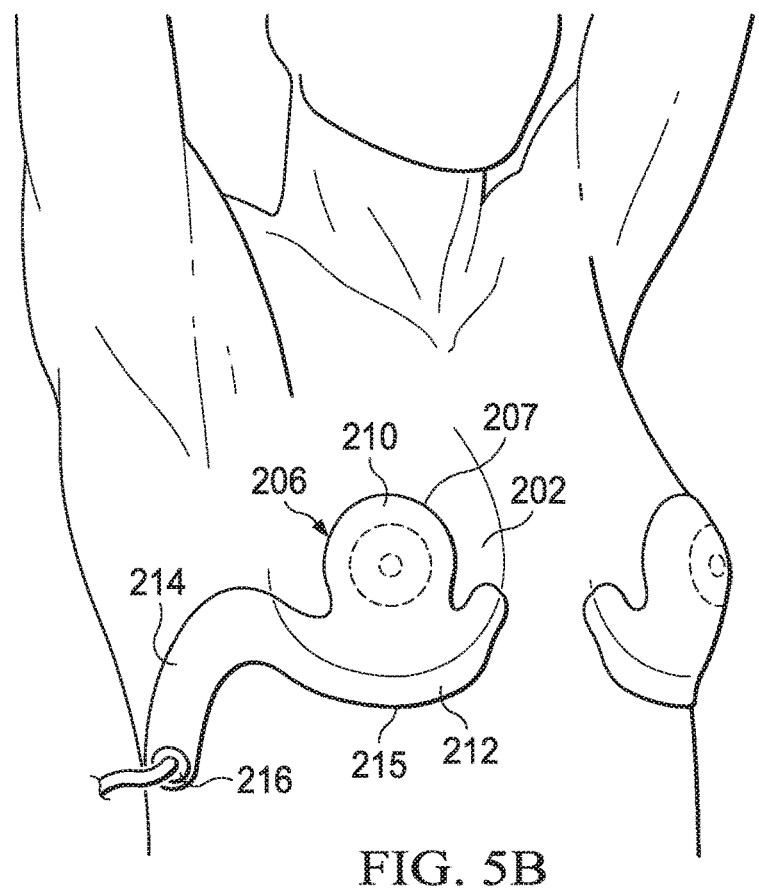
FIG. 5B is a side view of one of the example breast dressings applied to the breasts of a model simulation patient of FIG. 5A, according to one example illustrative embodiment.

The next several figures illustrate how various embodiments of the components and features associated with the therapy system 100 may be applied and operated. FIG. 5A and FIG. 5B illustrate example embodiments of dressings, such as the dressing 106, applied to a simulation patient 200. More specifically, FIGS. 5A and 5B illustrate how dressings may be applied to both a first breast 202 and a second breast 204 of the simulation patient 200. As shown in FIG. 5A, a first dressing 206 may be applied to the first breast 202 of the patient, and a second dressing 208 may be applied to the second breast 204. As can be seen in FIG. 5A, both the first dressing 206 and the second dressing 208 are respectively applied over portions of the first breast 202 and the second breast 204 which include the nipples, areolas and surrounding areas, as well as substantial semi-circle-shaped lower portions of the breasts and inframammary folds.

Referring now primarily to FIG. 5B, additional details of the first dressing 206 of FIG. 5A are shown. For example, the first dressing 206 may comprise multiple sections or regions, each of which may be tailored for a unique purpose. For example, the first dressing 206 may include a crown 210, an arm 212, and a bridge 214. The crown 210 may comprise one or more edges configured to conform to contours of a tissue site. For example, the crown 210 in the embodiment of FIG. 5B comprises a semi-circular or convex edge 207, which may typically be applied to a center portion of a breast, such as the first breast 202, and may cover structures such as the nipple, areola, and surrounding areas, which may include wound tissue. The arm 212 may be sized and shaped to conform to a lower portion of a breast, such as along the inframammary fold. In some embodiments, the arm 212 may have at least one contoured edge adapted to conform to contours of the first breast 202. For example, as illustrated in the embodiment of FIG. 5B, the arm 212 may have a convex edge 215 opposite the crown 210. In some embodiments, the arm 212 may be in the shape of a semi-circle or arc, and may be applied to the lower portion of the circumference of a breast, such as the first breast 202, and may abut the lower portion of the crown 210 of the first dressing 206. In some embodiments, the arm 212 may be substantially linear, with straight edges. In some embodiments, each end of the arm 212 may be arcuate shaped. Additionally, in some embodiments, the arm 212 may include a first, or lower, edge that is substantially straight, and a second, or upper, edge that is curved or arcuate. In some embodiments, the second, or upper, edge may extend away from the first, or lower, edge. Alternatively, the second, or upper, edge may be curved downward towards the first, or lower, edge. For example, in application, the first, or lower, edge may span beneath and/or along the inframammary fold, and the second, or upper, edge may extend across a curved portion of the breast. Furthermore, the arm 212 of the first dressing 206 may have a medial portion which spans from the center of a patient's chest, such as the intermammary cleft and around the lower portion of the first breast 202 to a lateral portion for extending to the side of the patient's torso, where the arm 212 meets the bridge 214.

The bridge 214 may be joined to the arm 212 of the first dressing 206 at a lateral portion of the arm 212. In some embodiments, the bridge 214 may join with the arm 212 to form approximately a 90 degree angle. In additional embodiments, the geometry of the first dressing may be altered to accommodate patients having different body proportions, and, for example, the bridge 214 may form a greater or smaller angle with the arm 212 of the first dressing 206. The bridge 214 may provide a continuous negative-pressure fluid pathway to transport fluids from the other portions of the first dressing 206, such as the crown 210 and the arm 212 of the first dressing 206. For example, the bridge 214 may provide a pathway to an interface, such as the dressing interface 216, which may be positioned on an end of the bridge 214 which is opposite the point where the bridge 214 connects to the arm 212. The dressing interface 216 may be fluidly connected to a pouch or other container through a tubeset, for removal and storage of fluids such as exudates. In some embodiments, the first dressing 206 may be formed as a single, continuous structure; however, embodiments may exist where different portions of the first dressing 206 may be constructed as separate sections, which may then be joined together either at or before application of the dressing to a tissue site.

Figure 6A:
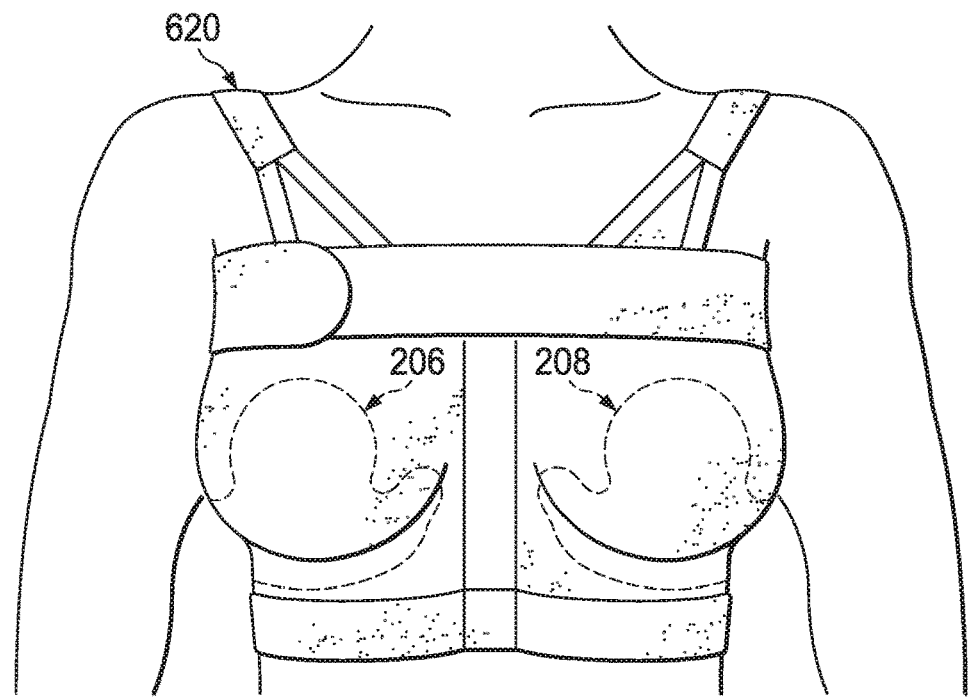
FIG. 6A is a front-facing view of an example compression garment worn over example breast dressings applied to the breasts of a model simulation patient, according to an example illustrative embodiment.
Figure 6B:
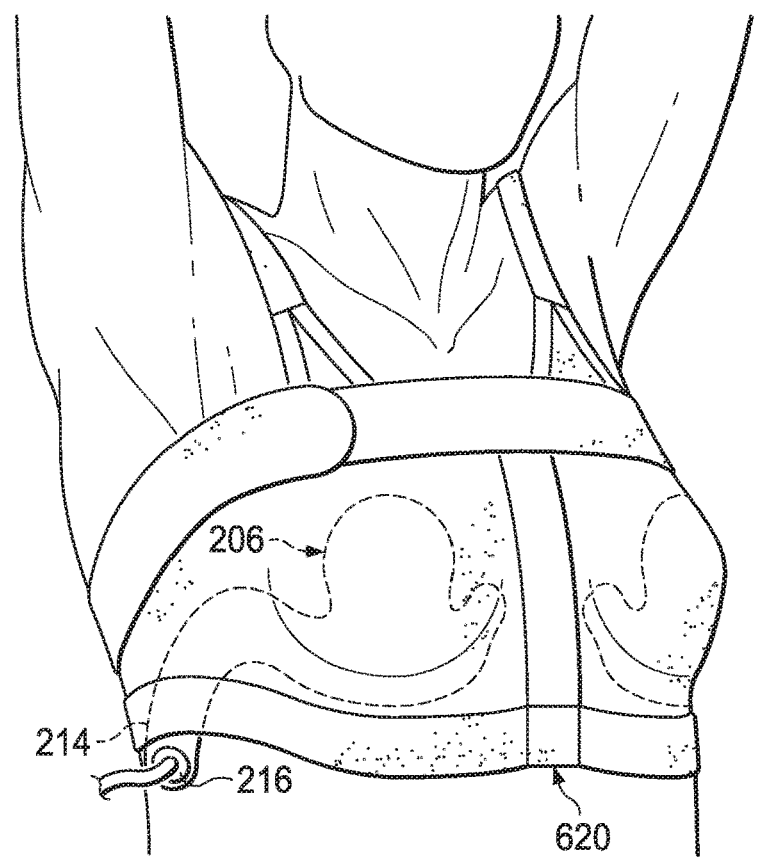
FIG. 6B is a side view of the example compression garment of FIG. 6A, worn over the example breast dressings, according to an example illustrative embodiment.

FIGS. 6A-6B illustrate how the components of a dressing subsystem, including a dressing, may be particularly suited for wearing under conventional compression garments, which are designed to aid healing. As shown in FIG. 6A, a first dressing 206 and second dressing 208 may each be applied to one of a patient's breasts with compression garment 620 worn over the two dressings. In some illustrative embodiments, the compression garment 620 may be a Juliet surgical bra with a Mammary Strap, both of which may be commercially available from Medical Z® of Houston, TX, USA. The low-profile breast dressings, such as first dressing 206 and second dressing 208, may each provide an open manifold pathway and exudate management capabilities while under compression by the compression garment 620. Moreover, the compression garment 620 may assist with anchoring the breast dressings to the patient. As can be seen in FIG. 6B, the dressings, such as first dressing 206 may be designed so that the fluid interface of the dressing for connecting to a tubeset remains accessible while the compression garment is worn. For example, the bridge 214 of the first dressing 206 may extend beyond an exterior border of the compression garment 620, so that the portion of the bridge 214 which includes the dressing interface 216 may be accessible to a user. Thus, the first dressing 206 may be fluidly coupled and decoupled to other components of the therapy system 100, particularly the pouch 108 of the dressing subsystem 102, without having to necessarily remove or reposition the compression garment 620.

Figure 7B:
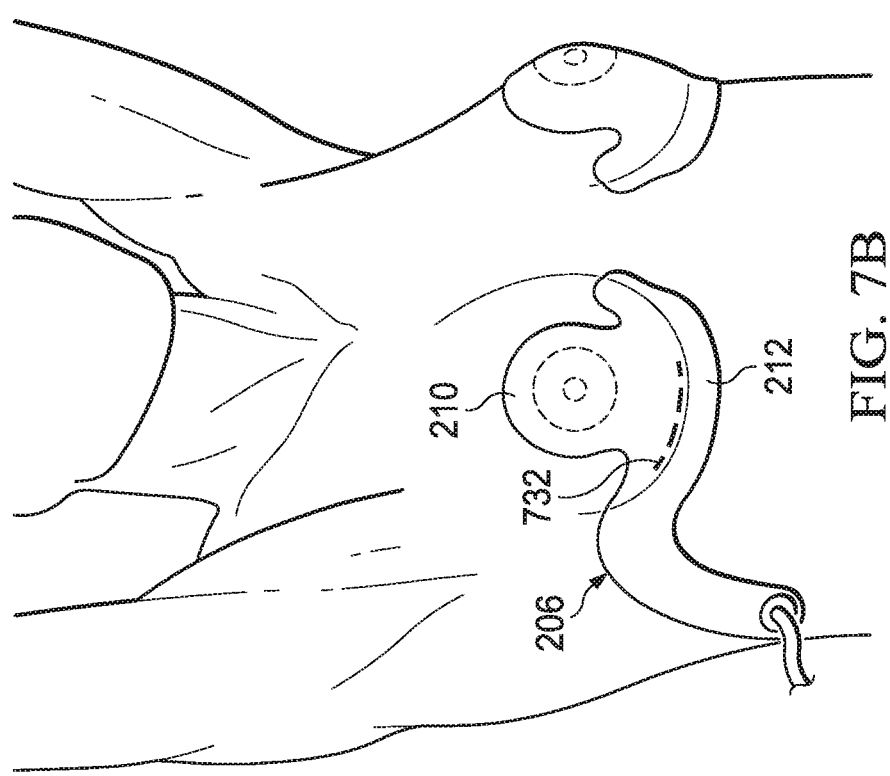
FIG. 7B is an overlay view of an example breast dressing applied over an incision on a breast, associated with some breast enhancement procedures, according to another example illustrative embodiment.
Figure 7A:
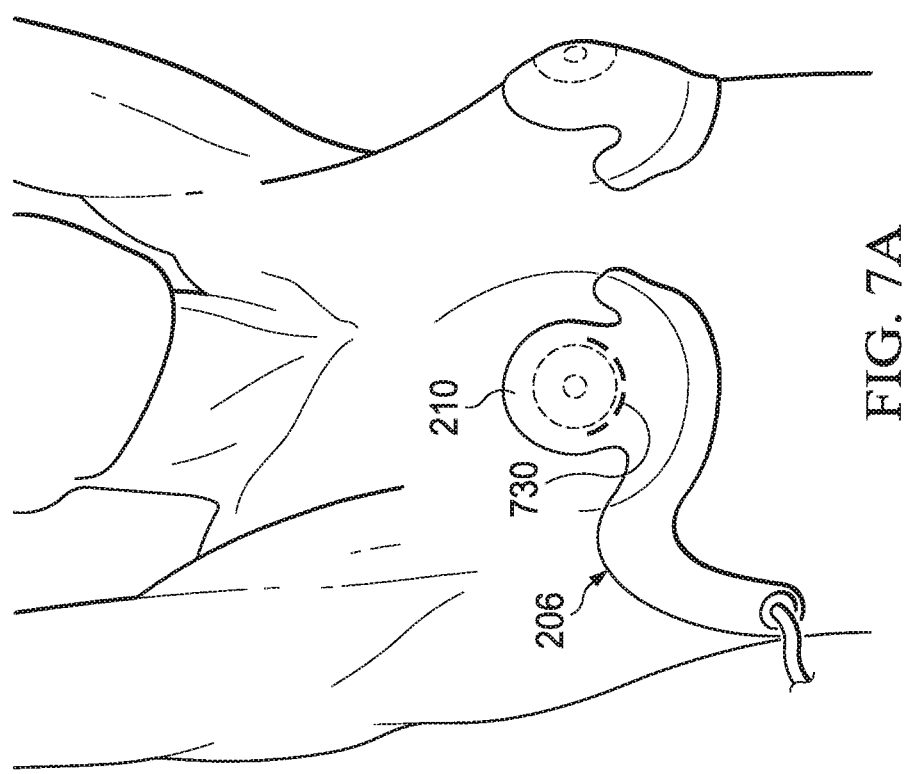
FIG. 7A is an overlay view of an example breast dressing applied over an incision on a breast, associated with some breast enhancement procedures, according to one example illustrative embodiment.
Figure 7C:
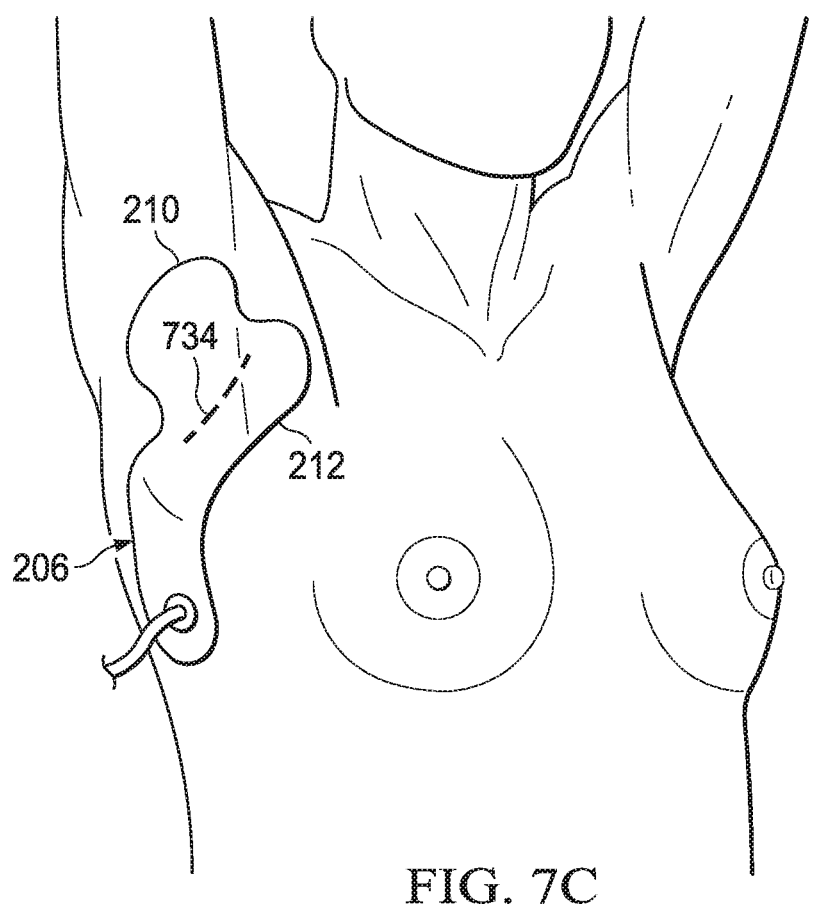
FIG. 7C is an overlay view of an example dressing applied over an incision located underneath the arm of a patient, associated with some breast enhancement procedures, according to yet another example illustrative embodiment.

FIGS. 7-9 illustrate how embodiments of the disclosed dressings may accommodate different sizes and shapes of incisions located on breast tissue of a patient. FIGS. 7A-7C illustrate example embodiments of the first dressing 206 applied to a variety of incisions, which may be characteristic of procedures for breast augmentation. For example, FIG. 7A provides an overlay view of a first dressing 206 applied over a peri-areolar incision 730. In this example application, the peri-areolar incision 730 may be covered by the crown 210 of the first dressing 206. To accommodate varying incision sizes, such as that of the peri-areolar incision 730, as well as overall variances in breast sizes, either or both of the crown 210 or the overall first dressing 206 may be offered in a variety of sizes. Referring now to FIG. 7B, a similar overlay view of a first dressing 206 applied to a breast incision is shown. In this example illustration, the first dressing 206 is applied over an inframammary incision 732, with the arm 212 of the first dressing 206 covering the inframammary incision 732. Similarly to the crown 210 of the first dressing 206, the arm 212 may be offered in a range of sizes to accommodate different incision lengths as well as different breast sizes. FIG. 7C provides an additional overlay view of a first dressing 206 applied over a transaxillary incision 734 located in the tissue under the arm. In this example application, the transaxillary incision 734 may be covered substantially by the arm 212 of the first dressing 206. In some embodiments, the first dressing 206 may be applied to such a transaxillary incision 734 by rotating the first dressing 206 up to approximately 90 degrees as compared to the position of the first dressing showed in FIGS. 7A-7B so that the arm 212 of the first dressing 206 is oriented generally inline with the sternum of the patient. Additionally, in some embodiments, a different dressing profile may be used to treat such a transaxillary incision 734, with a portion of the first dressing 206 wrapped around towards the side of a patient's torso. Furthermore, modified versions of the first dressing 206, as well as additional shapes of dressings may be applied as necessary to provide an appropriate fit and coverage of under-arm incisions, such as the transaxillary incision 734.

Figure 8A:
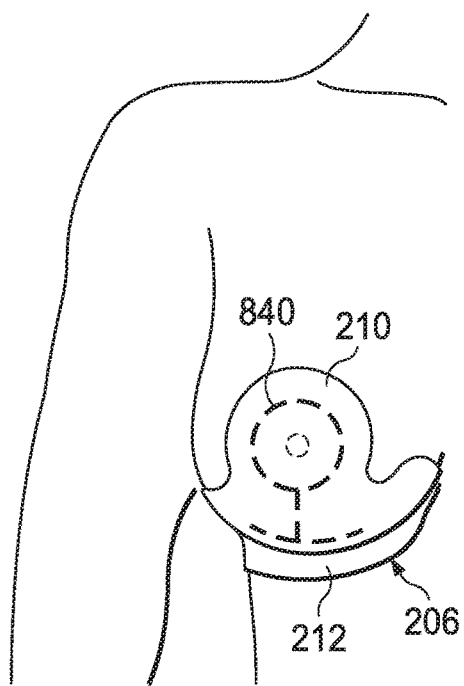
FIG. 8A is an overlay view of an example breast dressing applied over an incision on a breast, associated with some breast reduction procedures, according to another example illustrative embodiment.
Figure 8C:
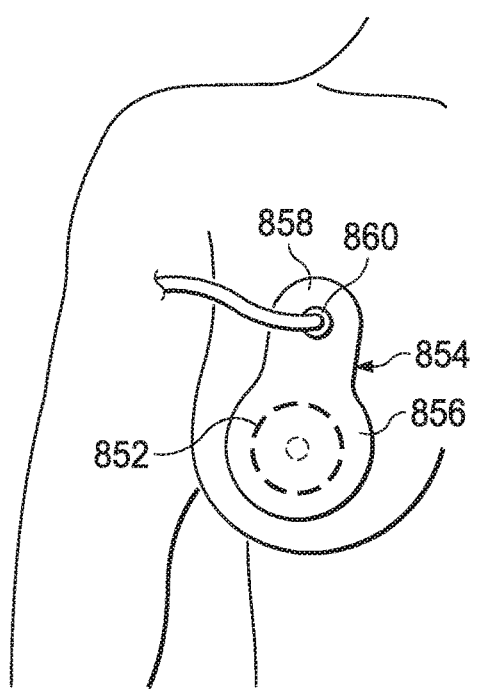
FIG. 8C is an overlay view of an example embodiment of a breast dressing applied over an incision on a breast, associated with some breast reduction procedures, according to yet another example illustrative embodiment.
Figure 8B:
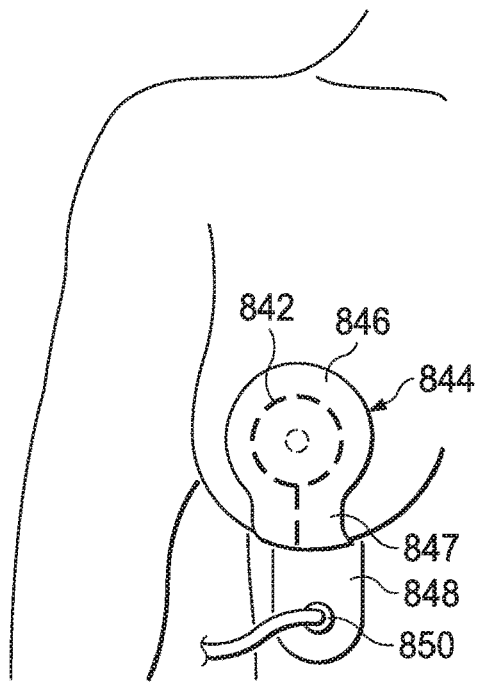
FIG. 8B is an overlay view of an example breast dressing applied over an incision on a breast, associated with some breast reduction procedures, according to another example illustrative embodiment.

FIGS. 8A-8C show additional applications of breast dressings, and how the breast dressings may be further applied to a variety of typical incisions associated with breast reduction procedures. For example, FIG. 8A provides an overlay view of a first dressing 206 applied over an anchor-shaped incision 840, which is an incision shape commonly experienced as a result of breast reduction procedures. In this example application, portions of the anchor-shaped incision 840 may be covered by either the crown 210 or the arm 212 of the first dressing 206. The crown 210 and the arm 212 of the first dressing 206 of FIG. 8A may be provided in a range of sizes, in order to accommodate size, shape, and proportional differences among patients. FIG. 8D provides an additional schematic view of the first dressing 206 of FIG. 8A, according to some example embodiments, for the purpose of illustrating some possible dimensions of components of the first dressing 206. For example, the crown 210 may have a crown length 841 which may range from approximately 60 mm to 120 mm. In some embodiments, the crown length 841 may be approximately 90 mm. Additionally, the arm 212 may have an arm length 843 which may range from approximately 150 mm to 350 mm. In some embodiments, the arm length 843 may be approximately 250 mm. The arm 212 may also have an arm width 845, which in some embodiments may range from approximately 40 mm to 90 mm. In some embodiments, the arm width 845 may be approximately 65 mm. Furthermore, in some embodiments of the first dressing 206, the portion of the arm 212 that extends to one side of the crown 210 is longer than the portion of the arm 212 that extends to the other side of the crown 210. For example, a first arm portion 849 of the arm 212 adapted for placement across or along a lateral portion of a breast extending towards a side of a patient's body may be longer than a second arm portion 851 of the arm 212 adapted to be placed towards the midline, or intermammary cleft, of the patient's body. In some embodiments, a first arm portion length 855 of the first arm portion 849, which may originate at the point of the arm 212 where a vertical axis 853, which extends through and bisects the crown 210 passes through the arm 212, may range from approximately 75 mm to 250 mm. For example, the first arm portion length 855 may be approximately 150 mm.

FIG. 8B provides an overlay view of another example embodiment of a breast dressing, which may be applied to incisions having some particular shapes. In this illustration, a lollipop-shaped incision 842 is located on a breast tissue, which may have resulted from a lollipop breast reduction method. A dressing 844 is shown placed over the various portions of the incision, which may extend continuously around a circumference of the areola of the breast and further extend in a line downward from the bottom of the circular portion of the incision. Thus, the dressing 844 may include a crown 846, an arm 847, and a bridge 848. In this example, the crown 846 is coupled to a first end of the arm 847, and the bridge 848 is coupled to a second end of the arm 847. The crown 846 may be sized to cover and extend beyond the outer circumference of the areola, and thus the portion of the incision encircling the areola, while the arm 847 may be sized to cover the downward, linear portion of the incision. The dressing 844 may also include a dressing interface 850 positioned in a bottom region of the bridge 848. Lollipop-shaped dressings, such as the dressing 844, may be offered in a variety of sizes to accommodate aspects of breast tissue unique to individual patients. A dressing having the shape of dressing 106, as depicted in FIG. 2, may also be applicable to breast reduction procedures using lollipop-shaped incisions.

The dressing 844 of FIG. 8B may also be provided in a range of sizes to accommodate breast and/or other anatomical size differences among patients. FIG. 8E provides an additional schematic view of the dressing 844 of FIG. 8B, according to some example embodiments, which illustrates example dimensions of components of the dressing 844. For example, the crown 846 may have a crown length 857 which may range from approximately 60 mm to 120 mm, and in some embodiments, may be approximately 90 mm. Additionally, the arm 847 and the bridge 848 may each or both have a width 859, which may range from approximately 40 mm to 100 mm, and in some embodiments may be approximately 70 mm. Furthermore, the dressing 844 may have an overall, or total length 861 ranging from approximately 150 mm to 350 mm. In some embodiments, the total length 861 may be approximately 270 mm.

FIG. 8C also provides an overlay view of another example embodiment of a breast dressing, which may be applied to incisions having a variety of shapes, particularly those incisions that occupy a somewhat circular area of breast tissue. For example, in this illustration, a circular, or donut-shaped incision 852 is located on a breast tissue, which may have resulted from a breast reduction procedure. A dressing 854 is shown placed over the various portions of the incision, which may extend continuously around a circumference of the areola of the breast. Thus, the dressing 854 may primarily include a crown 856, which may be sized to cover and extend beyond an incision which may encircle the areola. The dressing 854 may also include a bridge 858, which may be directly coupled to the crown 856 and extend outwardly from the crown 856. The bridge 858 may include a dressing interface 860. The dressing 854 may be offered in a variety of sizes to accommodate a variety of individual patients. A variety of differently-shaped dressings may also be applicable to breast reduction procedures that result in donut-shaped incisions, including dressing 106 of FIG. 2.

The dressing 854 of FIG. 8C may also be provided in a range of sizes. As illustrated in the schematic view of the dressing 854 shown in FIG. 8F, example dimensions of components of the dressing 854 are discussed. For example, the crown 856 may have a crown length 863 ranging from approximately 60 mm to 120 mm, while in some embodiments, the crown length 863 may be approximately 90 mm. Additionally, the bridge 858 may have a width 865, which may range from approximately 40 mm to 100 mm, and in some embodiments may be approximately 70 mm. The dressing 854 may have a total length 867 ranging from approximately 150 mm to 300 mm, and in some embodiments, the total length 867 of the dressing 854 may be approximately 200 mm.

Figure 9A:
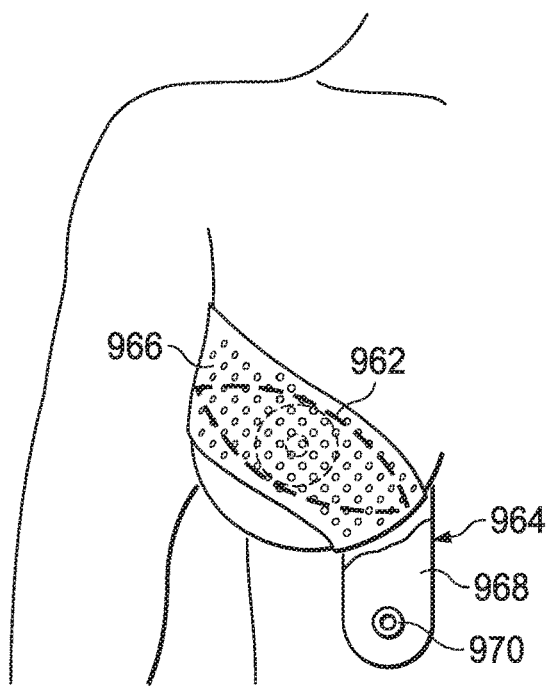
FIG. 9A is an overlay view of an example embodiment of a breast dressing applied over an incision on a breast, associated with some mastectomy procedures, according to one example illustrative embodiment.
Figure 9B:
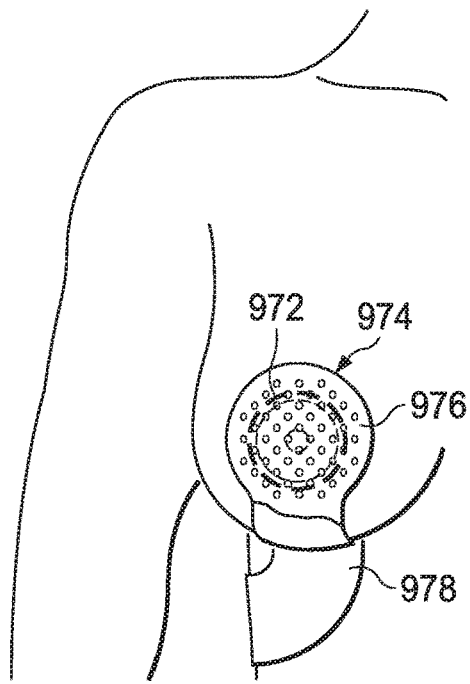
FIG. 9B is an overlay view of an example embodiment of a breast dressing applied over an incision on a breast, associated with some mastectomy procedures, according to another example illustrative embodiment.
Figure 9C:
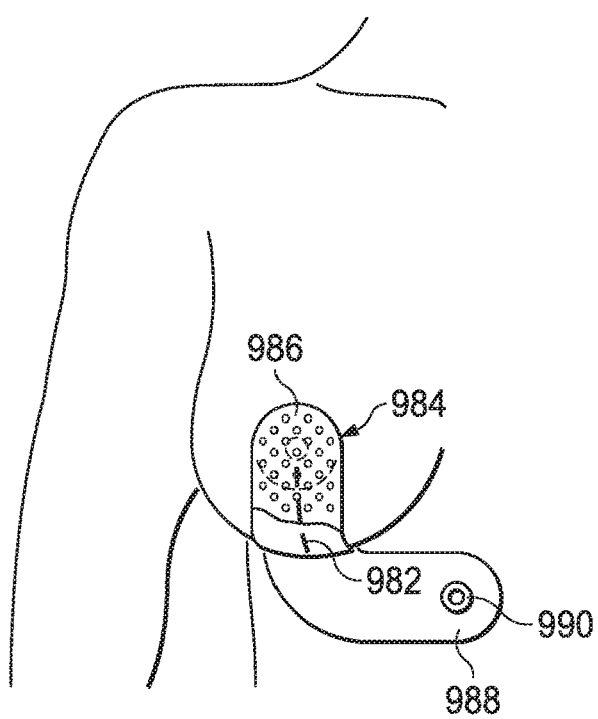
FIG. 9C is an overlay view of an example embodiment of a breast dressing applied over an incision on a breast, associated with some mastectomy procedures, according to yet another example illustrative embodiment.

FIGS. 9A-9C show further applications of example embodiments of breast dressings and how such dressings may be applied to a variety of incisions often associated with mastectomy procedures. For example, FIG. 9A provides an overlay view of a dressing applied over an incision that may be associated with a traditional mastectomy procedure. As shown in the figure, the mastectomy incision 962 may be performed in an oblong shape, spanning diagonally across the breast tissue and encompassing the nipple and areola. As a result, typically patients may be left with an incision running across the breast and towards the armpit, where lymph nodes may be located. In this example, mastectomy dressing 964 is shown placed over the areas of the breast tissue where the incision(s) may be made. The mastectomy dressing 964 may include an arm 966 and a bridge 968, each of which may be available in a variety of sizes. Dressings for use on breast tissue, such as mastectomy dressing 964, may also be offered in a variety of slightly different shapes, for example, such that the bend angle between the arm 966 and the bridge 968 may be varied to accommodate patients having different breast proportions. As depicted in FIG. 9A, the arm 966 of the mastectomy dressing 964 may include perforations on the patient-facing side of the mastectomy dressing 964 for communicating negative pressure to the breast tissue, and more specifically to the mastectomy incision 962. In this illustrative embodiment, when applied to a patient, the bridge 968 of the mastectomy dressing 964 may begin at a medial end of the arm 966 that may be located proximate to the intermammary cleft of the patient. The bridge 968 may extend vertically downward along the torso of the patient, with a dressing interface 970 positioned in a lower end section of the bridge 968. The dressing interface 970 may be used to fluidly couple the mastectomy dressing 964 to other components of the therapy system 100, such as pouch 108 or negative-pressure source 110.

Figure 9D:
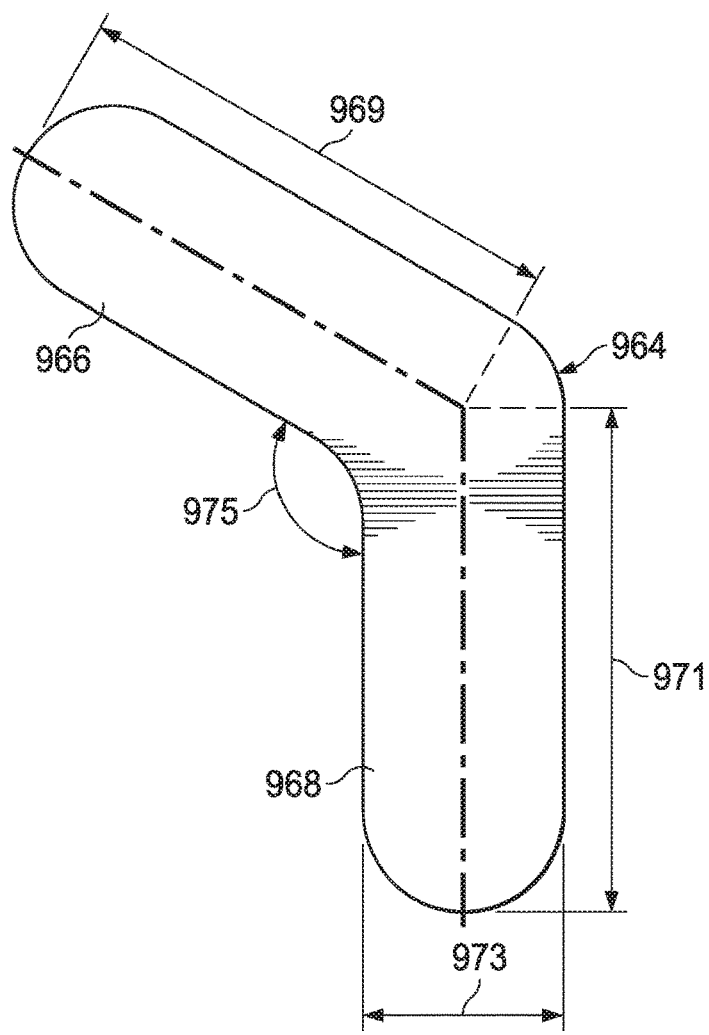
FIG. 9D is a schematic diagram illustrating additional details that may be associated with some embodiments of the dressing of FIG. 9A.

As previously discussed with respect to other embodiments, the mastectomy dressing 964 of FIG. 9A may be provided in a range of sizes to accommodate anatomical differences in size, shape, and proportions among patients. FIG. 9D provides an additional schematic view of the mastectomy dressing 964 of FIG. 9A, according to some example embodiments, which illustrates example dimensions of the mastectomy dressing 964. For example, the arm 966 may have an arm length 969 which may range from approximately 100 mm to 350 mm, and in some embodiments, may be approximately 220 mm. Additionally, the bridge 968 may have a bridge length 971 which may range from approximately 75 mm to 300 mm, and in some embodiments, may be approximately 165 mm. The bridge 968 may also have a bridge width 973, which may range from approximately 40 mm to 100 mm, and in some embodiments, may be approximately 70 mm. Additionally, as discussed with respect to FIG. 9A, a bend angle between the arm 966 and the bridge 968 may be varied to accommodate different patients. For example, the bend angle 975 may measure somewhere in the range of 100 degrees to 140 degrees. In some embodiments, the bend angle 975 may be approximately 120 degrees.

FIG. 9B provides an overlay view of another example embodiment of a breast dressing, which may be applied over an incision that may be associated with some alternative mastectomy procedures. As shown in the figure, the incision may be made in the tissue of the breast and may span around, or encircle, the nipple and areola, such as the case with skin-sparing mastectomy incision 972. Thus, when the skin-sparing mastectomy incision 972 is closed following the end of a mastectomy procedure, the skin-sparing mastectomy incision 972 may take the form of a somewhat circular incision located in approximately the center section of a breast. In this example embodiment, a dressing similar to mastectomy dressing 964 of FIG. 9A, more specifically reversed mastectomy dressing 974, is shown placed over the areas of the breast tissue where the incision may remain following the mastectomy procedure.

The reversed mastectomy dressing 974 may include a crown 976 and a bridge 978. As shown in FIG. 9B, the crown 976 may be placed over the skin-sparing mastectomy incision 972. The crown 976 of the reversed mastectomy dressing 974 may include perforations in a dressing tissue interface located on the patient-facing side of the reversed mastectomy dressing 974, which may facilitate the communication of negative pressure to the breast tissue, and more specifically to the skin-sparing mastectomy incision 972. In this illustrative embodiment, the bridge 978 of the reversed mastectomy dressing 974 may begin at a lower portion of the breast, below the crown 976. The bridge 978 may extend vertically downward to the bottom of the breast and further downward onto the patient's torso. The bridge 978 may then include a bend, or elbow, and may continue laterally towards the side of the patient's torso. A dressing interface (not shown) may be positioned on an end portion of the bridge 978 on the side of a patient's torso, which may be used for fluidly coupling the reversed mastectomy dressing 974 to the other components of the therapy system 100.

Figure 9E:
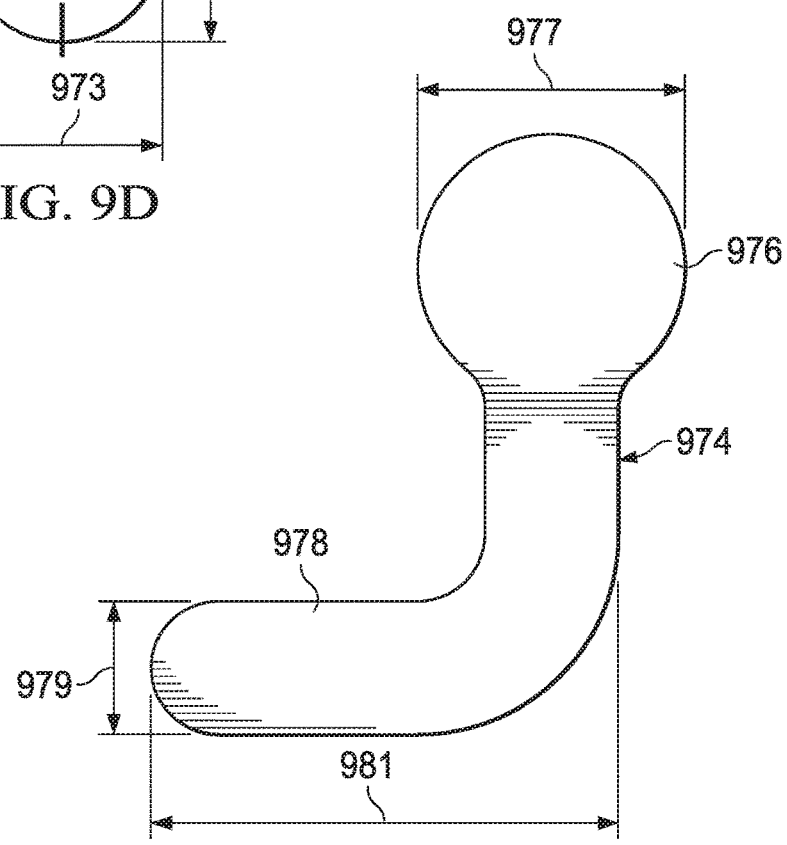
FIG. 9E is a schematic diagram illustrating additional details that may be associated with some embodiments of the dressing of FIG. 9B.

The reversed mastectomy dressing 974 of FIG. 9B may also be provided in a range of sizes. FIG. 9E provides an additional schematic view of the reversed mastectomy dressing 974 of FIG. 9B, according to some example embodiments, for illustrating example dimensions of the reversed mastectomy dressing 974. For example, the crown 976 of the reversed mastectomy dressing 974 may have a crown width 977, which may be a width of the crown 976 at its widest portion. In some embodiments, the crown width 977 may range from approximately 70 mm to 100 mm, and in some embodiments may be approximately 90 mm. Additionally, the bridge 978 of the reversed mastectomy dressing 974 may have a bridge width 979, which may range from approximately 50 mm to 90 mm, and in some embodiments may be approximately 70 mm. Furthermore, as discussed above, the bridge 978 may include a bend, or elbow, and include a portion that extends laterally towards the side of a patient's torso. In some embodiments, the portion of the bridge 978 that extends laterally may have a lateral bridge length 981 ranging from approximately 150 mm to 300 mm, and in some embodiments, may be approximately 220 mm.

FIG. 9C provides an overlay view of an additional example embodiment of a breast dressing, which may be applied over a type of incision associated with additional mastectomy procedures. For example, in this illustrative embodiment, a linear incision may be made on the breast tissue, which may begin at a bottom portion of the areola of the breast and may extend downwards to a bottom portion of the breast. Such a linear incision may be commonly performed in circumstances where it is desired to preserve the nipple, areola, and other portions of the patient's breast, as is represented by areola-sparing mastectomy incision 982. As illustrated in FIG. 9C, another variation of a mastectomy dressing, such as inverted mastectomy dressing 984, may be applied over the areola-sparing mastectomy incision 982. The inverted mastectomy dressing 984 may include an arm 986 and a bridge 988. The arm 986 may extend from an area surrounding the nipple and areola, and extend downward over the areola-sparing mastectomy incision 982. The arm 986 may include perforations in a dressing tissue interface located on the patient-facing side of the inverted mastectomy dressing 984 for facilitating negative-pressure communication with the areola-sparing mastectomy incision 982 and surrounding breast tissue. The bridge 988 of the inverted mastectomy dressing 984 may begin just below the bottom portion of the breast, adjacent to the end of the arm 986. The bridge 988 may extend medially towards the center of the patient's torso, where the bridge 988 may terminate in a portion of the torso below the intermammary cleft. A dressing interface, such as dressing interface 990 may be located on the end portion of the bridge 988.

Figure 9F:
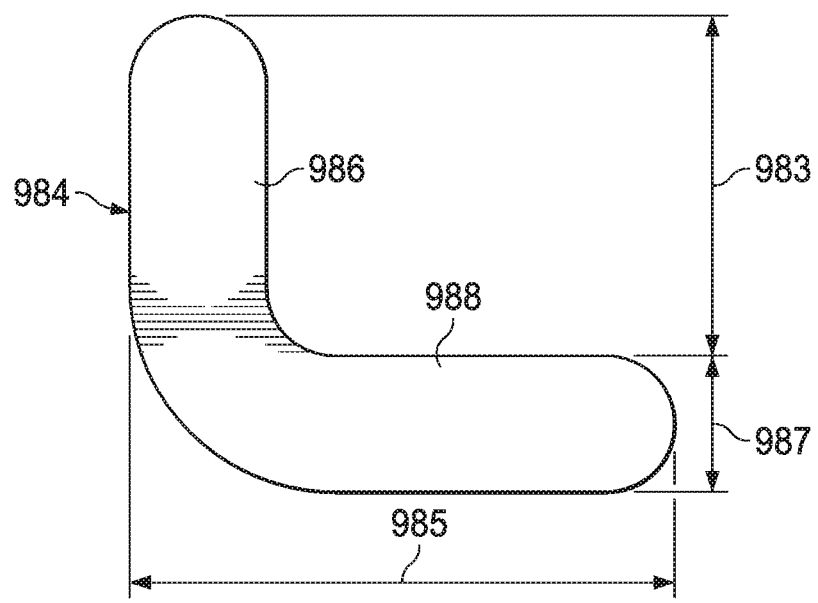
FIG. 9F is a schematic diagram illustrating additional details that may be associated with some embodiments of the dressing of FIG. 9C.

FIG. 9F provides a schematic view of the inverted mastectomy dressing 984 of FIG. 9C, and illustrates some example dimensions of the inverted mastectomy dressing 984. For example, the arm 986 may have an arm length 983 ranging from approximately 100 mm to 300 mm. In some embodiments, the arm length 983 may be approximately 200 mm. Additionally, the bridge 988 may have a bridge length 985 ranging from approximately 100 mm to 300 mm, and in some embodiments, may be approximately 250 mm. The bridge 988 may also have a bridge width 987, which may range from approximately 40 mm to 100 mm, and in some embodiments, may be approximately 70 mm.

Figure 10:
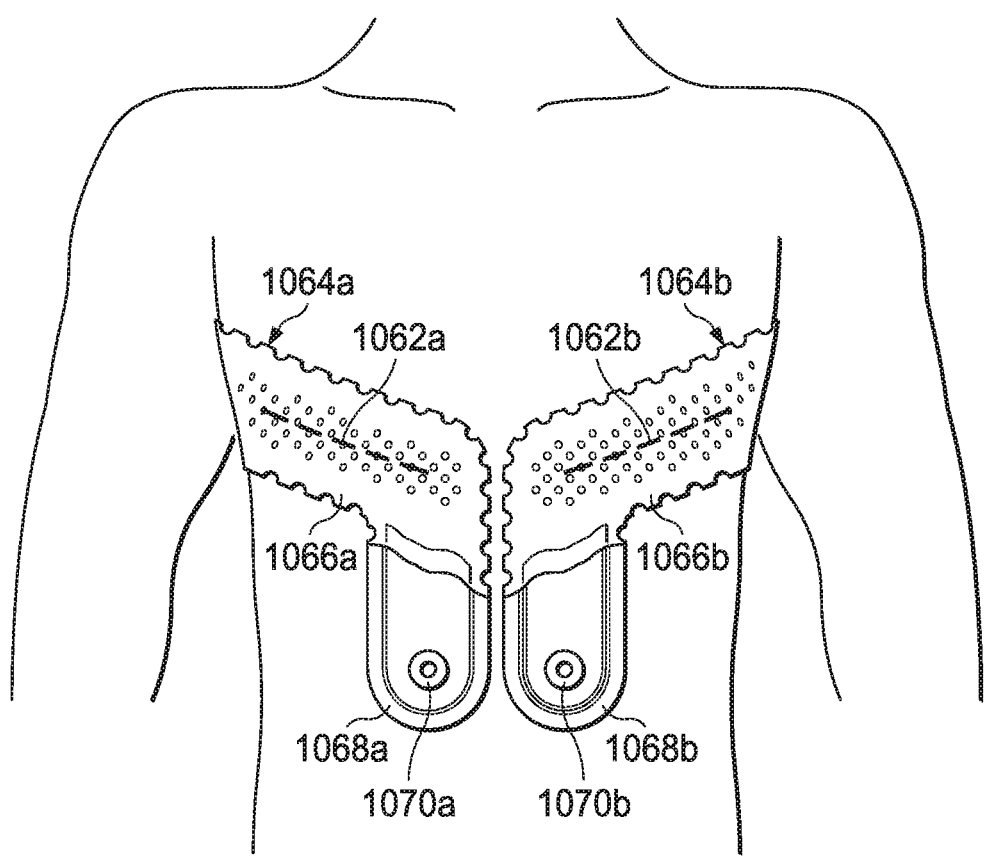
FIG. 10 is a front-facing view of example breast dressings applied to breasts over incisions associated with some mastectomy procedures, according to one example illustrative embodiment.

Referring now primarily to FIG. 10, an image of an example patient dressed with multiple dressings following a traditional double mastectomy procedure is shown. As seen in FIG. 10, following the procedure, the patient is left with two incisions, with each incision running across the respective breast and towards the location of lymph nodes and respective armpit. In this particular example, two dressings, mastectomy dressings 1064*a* and 1064*b*, which are similar to the mastectomy dressing 964 of FIG. 9A, are shown applied to the breasts of the patient. For example, mastectomy dressing 1064*a* is shown applied over mastectomy incision 1062*a* on a first breast, and mastectomy dressing 1064*b* is shown applied over mastectomy incision 1062*b* on a second breast. The various layers and materials of the dressings may be the same or substantially similar to the layers and materials described and illustrated with reference to FIG. 3. Similar to the other dressing embodiments previously discussed, each of the mastectomy dressings 1064*a* and 1064*b* may include an arm 1066*a* and 1066*b*, respectively, and a bridge 1068*a* and 1068*b*, also respectively. As shown, each of the bridges 1068*a* and 1068*b* may extend downward from the intermammary cleft along a center portion of the torso of the patient, with dressing interfaces 1070*a* and 1070*b* positioned in lower portions of each of the bridges 1068*a* and 1068*b*, respectively.

The mastectomy dressings may be used in conjunction with breast reconstruction procedures, since many patients may choose to have breast reconstructive surgery at the same time as the mastectomy. Usually, if the patient chooses to undertake reconstruction, a tissue expander may be inserted into the breast cavity and gradually filled with saline as the mastectomy incision heals and the surrounding tissue permits. Thus, it is also worth noting that the initial placement of mastectomy variants of the dressings disclosed herein, such as mastectomy dressings 1064, are likely to be on a flatter contour of the patient. The mastectomy-specific dressings, such as mastectomy dressings 1064, may also be used to treat breast incisions typically associated with breast enlargement procedures. Such enlargement incisions often may be located in the inframammary breast fold and may be linear and of shorter length.

In operation, the components of the dressing subsystem 102, the dressing 106 and the pouch 108, may be applied to the patient. The dressing 106 may be a wound-specific, or incision-specific, breast dressing, and thus in some cases, the type of breast dressing included as part of the dressing subsystem 102 may vary based on the particular breast treatment application. The dressing 106 may provide a sealed therapeutic environment proximate to a tissue site, such as an incision located on a breast tissue, substantially isolated from the external environment. A second breast dressing may also be applied to the patient, following which both dressings may be fluidly connected to the pouch 108. Importantly, in the case of multiple dressings, the dressings may be of the same or different size, shape, or design, depending on the specific therapeutic needs of each area of breast tissue to be treated. Additionally, there may be circumstances where a single dressing may be suitable for applying to at least a portion of both right and left breasts of a patient. A therapy unit, including a negative-pressure source, may then be fluidly coupled to the components of the dressing sub system 102.

In operation, the negative-pressure source can reduce the pressure in the sealed therapeutic environment provided by the dressing 106. Negative pressure applied across the tissue site in the sealed therapeutic environment can induce macrostrain and microstrain in the tissue site, as well as remove exudates and other fluids from the tissue site. As the dressing 106 comes into contact with fluids from the tissue site, such as an incision on a breast, the fluids may move through perforations of a dressing tissue interface layer and toward one or more manifold layers. The manifold layer(s) may wick or otherwise move the fluids through the dressing tissue interface and away from the tissue site. Thus, the dressing tissue interface may be adapted to communicate fluids from the tissue site rather than store the fluids. The manifold layer(s) therefore may be adapted to wick, pull, draw, or otherwise move fluids along the manifold layer(s) through the dressing 106, and towards a dressing interface having a dressing aperture. The fluids may then be drawn through the dressing aperture and into a dressing tubeset by the negative pressure. The fluids may then be transported to and collected in the pouch 108.

The systems, apparatuses, and methods described herein may provide significant advantages. For example, the disclosed therapy systems offer easy-to-apply and easy-to-use negative-pressure wound management solutions appropriate for use on the breast. Post-surgical breast wounds may benefit from the application of negative pressure as a bolster of the wound and for active removal of fluids which may be stored remotely for improved healing. For example, the unique components of the disclosed therapy systems, such as the dressing 106 and the pouch 108 of therapy system 100 may work in unison to provide the benefits of post-operation exudate management, incision management, and may assist with infection reduction. In contrast, current standards of care for breast wounds typically involve standard advanced wound dressings (AWDs) and drainage bulbs, which either require frequent changing or are cumbersome and interfere with the patient's quality of life. Thus, a contoured, manifolding, and absorbent structure, such as the dressing 106 disclosed herein, may be easily and readily applied by the patient and may deliver the beneficial effects of negative-pressure therapy, while minimizing obtrusiveness and visual implications for the patient, thus addressing this poorly-met need. Thus, unlike previous therapy systems and dressings in the field, the present systems and dressings offer both wound management and drainage management together, which would traditionally be managed by two or more different products, such as separate dressings and pressure drain bulbs. As compared to conventional "bulb" drain systems often used following surgical procedures, the disclosed therapy systems may offer significantly improved exudate management, partially due to the constant application of negative pressure. Furthermore, the dressings and pouches of the disclosed therapy systems allow for wound exudates to largely be stored away from the wound site, such as an incision on a breast, thus helping to reduce pressure points due to swelling of the one or more absorbent layers of the dressings. As a result, the dressings of the disclosed therapy systems may also be less obtrusive than conventional internal manifold drains. Additionally, as a result of the directional fluid wicking capabilities within some embodiments of the disclosed dressings, wound fluids may be moved away from the drainage site towards the collection point, such as a fluid interface of a dressing, even without the presence of airflow caused by the delivery of negative pressure. In some embodiments, drainage management in conjunction with closed wound management may also be enhanced through the "French Fry" method of using fingers of white-foam. In such a method, fingers of white-foam may be placed within the breast and surrounding tissue and may be orientated towards drainage locations identified by the surgeon. The white-foam fingers may protrude through the epidermis and may be pneumatically coupled to a dressing, such as the first dressing 206. Furthermore, the disclosed dressings may avoid applying apposition forces to wounds, which could otherwise be problematic for complex, multi-directional compound wounds. The absence of apposition forces may facilitate the cosmetic healing of complex and multi-directional incisions, as intended by a surgeon. Thus, the disclosed dressings may offer significant advantages for reducing or eliminating apposition forces over traditional negative-pressure wound therapy dressings utilizing collapsible foam. As a result, the proper cosmetic healing of multi-direction incisional wounds may be enhanced.

Additionally, the sealed wound environment, which may be achieved with the use of the disclosed dressings, may reduce infection rates of wound sites. Also, the incorporation of a silicone patient interface as part of the dressing 106 and the pouch 108, for example the dressing tissue interface 150 of the dressing 106 and the pouch tissue interface 156 of the pouch 108 may contribute to cosmetic scar reduction. On a related note, the adherent components of the disclosed therapy systems, such as dressing 106 and pouch 108, may provide for a low amount of trauma when removed. For example, the limited use of acrylic adhesive may allow for temporary retention of a dressing, such as dressing 106, during bra placement and changes, however may also allow for the dressing 106 to be moved without damaging the tissue site.

Also worth noting, the disclosed dressing and pouch assemblies may also be adapted to function with other disposable negative-pressure wound therapy systems, such as the SNAP™ systems, commercially available from Kinetic Concepts Inc., of San Antonio, TX, USA.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing subsystem 102, the therapy unit 104, or both may be eliminated or separated from other components for manufacture or sale.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for providing negative-pressure treatment, the system comprising:
    a first dressing assembly shaped for placement on a breast and comprising:
        a crown comprising a substantially circular section having a diameter and adapted to cover an areola, and
        an elongate arm having a medial portion forming a first end of the elongate arm and a lateral portion forming a second end of the elongate arm, the elongate arm adapted to cover a wound site along an inframammary fold, wherein the first dressing assembly further comprises:
a dressing tissue interface formed from a silicone adhesive, the dressing tissue interface comprising a first surface adapted to adhere to the breast and comprising perforations,
a dressing manifold having a first side and a second side, wherein the first side of the dressing manifold is disposed against a second surface of the dressing tissue interface, and
a dressing cover disposed on the second side of the dressing manifold and having an adhesive border for sealing the dressing manifold and the dressing tissue interface to the breast;
a bridge extending from the second end formed by the lateral portion of the elongate arm, the bridge being perpendicular to the elongate arm;
wherein each of the crown, the elongate arm, and the bridge comprises a portion of the dressing tissue interface, the dressing manifold, and the dressing cover;
a second dressing assembly;
an absorbent pouch comprising a first port configured to be in fluid connection with the first dressing assembly, a second port adapted for receiving negative pressure, and a third port configured to fluidly connect the second dressing assembly to an interior of the absorbent pouch; and
a negative-pressure port positioned on the first dressing assembly and configured for fluid communication with a negative-pressure source.

2. The system of claim 1, wherein the first dressing assembly further comprises a connector positioned proximate to a lateral terminus of the bridge.

3. The system of claim 1, wherein the perforations consist of a first plurality of holes in the crown and a second plurality of holes in the elongate arm.

4. The system of claim 2, wherein the dressing manifold comprises a plurality of fibers oriented towards the lateral terminus of the bridge.

5. The system of claim 4, wherein the plurality of fibers are oriented towards the connector.

6. The system of claim 1, wherein the silicone adhesive is a low-tack silicone adhesive.

7. The system of claim 1, wherein the first dressing assembly and the second dressing assembly comprise different geometries.

* * * * *